United States Patent [19]

Iwanami et al.

[11] 4,404,373
[45] Sep. 13, 1983

[54] PROCESS FOR THE PREPARATION OF 7α-METHOXY-7β-(1,3-DIETHIETANE-2-CARBOXAMIDO)CEPHALOSPORANIC ACID DERIVATIVES

[75] Inventors: Masaru Iwanami, Yokohama; Tetsuya Maeda, Urawa; Yoshinobu Nagano, Niiza; Masaharu Fujimoto, Tokyo; Noriaki Nagano, Ageo; Atsuki Yamazaki, Ichikawa, all of Japan

[73] Assignee: Yamanouchi Pharmaceutical Co., Ltd., Tokyo, Japan

[21] Appl. No.: 208,298

[22] Filed: Nov. 19, 1980

Related U.S. Application Data

[62] Division of Ser. No. 913,500, Jun. 7, 1978, Pat. No. 4,263,432.

[30] Foreign Application Priority Data

Jun. 10, 1977 [JP] Japan .................................. 52-68699
Jul. 28, 1977 [JP] Japan .................................. 52-90772
Feb. 2, 1978 [JP] Japan .................................. 53-10772

[51] Int. Cl.³ .................... C07D 501/57; A61K 31/54
[52] U.S. Cl. ..................................... 544/21; 424/246; 544/27

[58] Field of Search .......................... 544/21; 424/246

[56] References Cited

U.S. PATENT DOCUMENTS

| 3,516,997 | 6/1970 | Takano et al. | 544/27 |
|---|---|---|---|
| 4,007,176 | 2/1977 | Berger et al. | 544/27 |
| 4,008,246 | 2/1977 | Ochiai et al. | 544/27 |
| 4,198,339 | 4/1980 | Iwanami et al. | 544/21 |
| 4,203,899 | 5/1980 | Ochiai et al. | 544/21 |
| 4,263,432 | 4/1981 | Iwanami et al. | 544/27 |
| 4,299,829 | 11/1981 | Kamiya et al. | 544/21 |
| 4,182,8680 | 1/1980 | Ochiai et al. | 544/21 |

Primary Examiner—Nicholas S. Rizzo
Attorney, Agent, or Firm—Burgess, Ryan & Wayne

[57] ABSTRACT

The invention relates to novel 7α-methoxycephalosporin derivatives having at the 7β-position an amido group acylated by a 1,3-dithietane carboxylic acid residue and to 7β-isothiazolylthioacetamido-7α-methoxycephalosporins having antibacterial activity by themselves and, as the case may be, capable of being converted into the aforesaid 7α-methoxycephalosporin derivatives. The compounds of this invention exhibit excellent antibacterial activity and are particularly effective against gram negative bacteria.

2 Claims, No Drawings

PROCESS FOR THE PREPARATION OF 7α-METHOXY-7β-(1,3-DIETHIETANE-2-CARBOX-AMIDO)CEPHALOSPORANIC ACID DERIVATIVES

This is a division of application Ser. No. 913,500, filed June 7, 1978 now U.S. Pat. No. 4,263,432.

BACKGROUND OF THE INVENTION

1. Field of the Invention

This invention relates to a novel series of cephalosporin compounds having antibacterial activity and to intermediates useful for preparing them. To the best of our knowledges, the compounds of this invention disclosed herein are novel.

2. Description of the Prior Art

In the past several decades various antibiotics have been investigated and used for the treatment of various infectious diseases of animals including men but since resistant bacteria appear in many cases, there are some infectious diseases which have not been treated by known antibiotics. Moreover, new antibiotics are constantly being sought in order to supplement and expand the physicians' armamentarium, particularly for the treatment of infections involving pathogens which have become resistant to the chemotherapeutic agents now in use.

Various cephalosporins have been known and a number of disclosures such as German Offenlegungsschrift No. 2,356,388 disclose a variety of cephalosporins or heterocyclic acyl groups very broadly but none of them specify the compounds of this invention.

SUMMARY OF THE INVENTION

According to this invention, there are provided the novel cephalosporins represented by general formula I

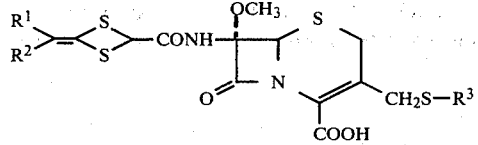

wherein $R^1$ represents a carboxyl group or a functional derivative residue thereof; $R^2$ represents a hydrogen atom, a lower alkyl group, a lower alkoxy group, a lower alkanoyl group, $R^4S(O)_n$ group (wherein $R^4$ represents a lower alkyl group and n represents 0, 1, or 2), an aryl group, an aroyl group, a carboxyl group, a functional derivative group of a carboxyl group, a lower alkenyl group, a sulfamoyl group, or a heterocyclic residue; and $R^3$ represents a lower alkyl-substituted tetrazolyl group or a lower alkyl-substituted thiadiazolyl group, and the pharmaceutically acceptable salts thereof.

The cephalosporin compounds of this invention have excellent antibacterial activity, particularly against gram negative bacteria.

The invention also provides various processes for preparing the aforesaid cephalosporin compounds for general formula I.

DESCRIPTION OF THE PREFERRED EMBODIMENTS

Now, the functional derivative residue of carboxyl group represented by $R^1$ or $R^2$ of general formula I means, for example, a carboxylic acid lower alkyl ester residue, a carboxylic acid aralkyl ester residue, a carbamoyl group, a carbazoyl group ($NH_2NHCO-$), a cyano group, etc. Also, the lower alkyl group in the general formula is a straight chain or branched alkyl group having 1–4 carbon atoms, such as methyl group, ethyl group, isopropyl group, n-butyl group, tert-butyl group, etc.

Examples of the aryl group are phenyl group, naphthyl group, etc. Examples of the aroyl group are benzoyl group, naphthoyl group, etc.

$R^3$ of general formula I represents, as described above, a lower alkyl-substituted tetrazolyl group or a lower alkyl-substituted thiadiazolyl group, and examples of the tetrazolyl group are a 1H-tetrazol-5-yl group, 2H-tetrazol-5-yl group, etc., and examples of the thiadiazolyl group are a 1,3,4-thiadiazolyl group, a 1,2,5-thiadiazolyl group, a 1,2,4-thiadiazolyl group, etc.

Furthermore, the groups and residues represented by $R^1$, $R^2$, $R^3$ and $R^4$ of general formula I may have been substituted when they can have substituents. For example, examples of the substituted groups or residues are an N-monoalkylcarbamoyl group, an N-dialkylcarbamoyl group, and an alkoxycarbonylamino group for $R^1$ a hydroxyalkyl group, a carboxyalkyl group, an alkoxyalkyl group, an arylalkyl group, a hydroxyphenyl group, and an alkoxyphenyl group for $R^2$; and an alkylthio-substituted thiadiazolyl group, for $R^3$, etc.

The compounds of this invention belong to 7-methoxycephalosporin derivatives as shown by general formula I and the most specific feature of the compounds is that the acyl group at the 7β-position originates in 4-substituted methylene-1,3-dithietane-2-carboxylic acid. The acylation by 4-membered ring carboxylic acid has not hitherto been known in the field of cephalosporin chemistry and, in particular, the 1,3-dithietanecarboxylic acid itself used in one of the processes for preparing the compounds of this invention shown below is a novel compound which has not been disclosed in any literatures.

The objective compounds of this invention are prepared by the following various processes:

PROCESS 1

In the process, the compounds of this invention shown by general formula I are prepared by reacting 4-substituted methylene-1,3-dithietanecarboxylic acid represented by general formula II

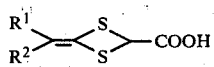

wherein $R^1$ and $R^2$ have the same significance as in general formula I and 7β-amino-7α-methoxy-3-heterocyclic thiomethyl-Δ³-cephem-4-carboxylic acid represented by general formula III

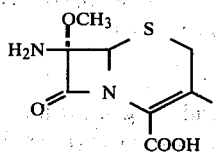

wherein $R^3$ has the same significance as in general formula I.

In the reaction of the compounds of general formula II and the compounds of general formula III, the compounds may be caused to react directly with each other in the presence of a condensing agent such as N,N'-dicyclohexylcarbodiimide, etc., but it is suitable to use the compound of formula II after introducing known protective groups to $R^1$ and $R^2$ according to the properties of $R^1$ and $R^2$ and also the compounds of formula III after introducing a known protective group to the carboxyl group at the 4-position. For example, when $R^1$ and/or $R^2$ of the compound of formula II is a carboxyl group, the carboxyl group of the compound and also the carboxyl group at the 4-position of the compounds of formula III are protected beforehand by a triphenylmethyl group, a tert-butyl group, a benzhydryl group, etc., and further the carboxylic acid at the 2-position of the compound of formula II or the amino group at the 7β-position of the compound of formula III are converted into the reactive derivatives prior to performing the reaction. Preferred examples of the reactive derivative of the carboxylic acid are an acid halide, a mixed acid anhydride, an active ester, an active amide, an acid anhydride, an acid azide, etc.

The compounds of general formula II are novel compounds and they are obtained by reacting 2,2'-substituted ethylene-1,1-dithiol represented by general formula IV

    IV wherein $R^1$ and $R^2$ have the same significance as in general formula I and dihalogenoacetic acid or the lower alkyl ester thereof represented by general formula V

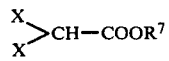    V wherein X represents a halogen atom and $R^7$ represents a hydrogen atom or a lower alkyl group and then, when the compound of formula V is the lower alkyl ester, replacing the alkyl or converting it to a reactive derivative.

The reaction of the compounds of formula II and the compounds of formula III or the reactive derivative thereof is usually carried out in an inert solvent under heating or cooling but in order to avoid the epimerization of the methoxy group at the 7α-position during the reaction, it is preferred to perform the reaction at low temperature, particularly at temperatures below −20° C.

The compound thus formed can be converted into the compounds of formula I by removing the protective group or groups in an ordinary manner.

PROCESS 2

In the process, the compounds of general formula I are prepared by reacting 3-acetoxymethyl- or 3-carbamoyloxymethyl-7β-(4-substituted-1,3-dithietanecarboxamido)-7α-methoxy-Δ³-cephem-4-carboxylic acid represented by general formula VI

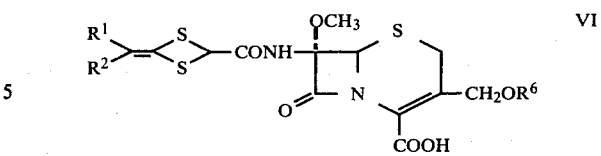    VI wherein $R^1$ and $R^2$ have the same significance as in general formula I and $R^6$ represents an acetyl group or a carbamoyl group and the heterocyclic thiol represented by general formula VII $R^3$—SH    VII wherein $R^3$ has the same significance as in general formula I or the alkali metal substitute thereof at the hydrogen atom of the mercapto group.

The reaction is performed at room temperature or under heating usually in an inert solvent. Examples of the inert solvent are acetone, dimethylformamide, methanol, ethanol, water, and a phosphate buffer and, if necessary, they are used as a mixture of them. When a compound of general formula VII is used in the free state, it is preferred to perform the reaction in the presence of a base such as an alkali metal hydroxide, an alkali metal carbonate, an alkali metal hydrogencarbonate, trialkylamine, pyridine, dimethylaniline, etc. After the reaction is over, the compound of formula I formed is isolated by acidifying the reaction mixture and recovering the precipitates thus formed or by subjecting the reaction mixture to a solvent extraction.

In addition, a compound of formula VI used in the process can be obtained by reacting a compound of general formula II used in Process 1 and 7β-amino-7α-methoxycephalosporanic acid ($R^6$ in the formula is acetyl group) or 7β-amino-3-carbamoyloxymethyl-7α-methoxy-Δ³-cephem-4-carboxylic acid ($R^6$ in the formula is -CONH₂) represented by general formula VIII

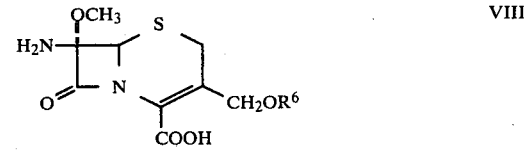    VIII wherein $R^6$ has the same significance as in general formula VI under similar reaction condition as in Process 1.

PROCESS 3

A compound of this invention shown by general formula I is also obtained by treating the 7α-methoxy-3-heterocyclic thiomethylcephalosporin derivative represented by general formula IX

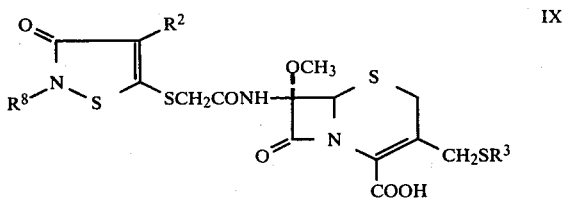    IX wherein $R^2$ and $R^3$ have the same significance as in general formula I and $R^8$ represents a hydrogen atom or a substituted or unsubstituted alkyl group under a basic condition.

In addition, when $R^8$ of general formula IX is hydrogen, the derivative of the formula includes the tautomer of the following formula

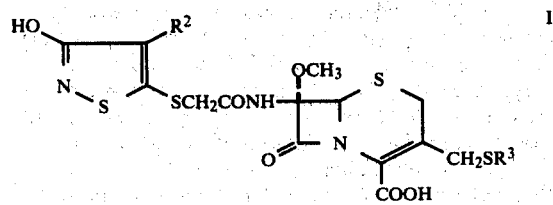

wherein $R^2$ and $R^3$ are the same as above.

Proper bases used in this process are weak bases such as sodium-hydrogen-carbonate, potassium hydrogen-carbonate, sodium carbonate, etc. The reaction is usually performed in a solvent at room temperature or under cooling. Any solvents which do not affect the reaction may be used but preferably water or an organic solvent which are miscible with water, such as methanol, acetone, tetrahydrofuran, dimethylformamide, etc., are used singly or in a combination thereof. The isolation and purification of the product from the reaction mixture are performed by a conventional manner such as extraction with organic solvent, crystallization, column chromatography, etc.

The compounds of general formula IX used in the process exhibit an excellent antibacterial activity per se and are also useful as intermediates for the preparation of compounds of formula I. Therefore, another object of this invention is to provide the intermediate compounds which have excellent antibacterial activity and are useful for the production of the compounds of formula I and also to provide a process of preparing the intermediate compounds.

The compounds of general formula IX are prepared by, for example, the following processes:

PROCESS A

The compounds of general formula III may be reacted with a corresponding isothiazolylthioacetic acid or the reactive derivative thereof according to Process 1 of this invention. That is, the reaction is usually performed in an inert solvent such as, preferably, acetone, chloroform, methylene chloride, ethylene chloride, tetrahydrofuran, dimethylformamide, acetonitrile, ethyl acetate, ethyl formate, etc. These solvents may be used singly or in a combination thereof, or, if the solvent is water-soluble, the solvent can be used as a mixture with water if no hindrance occurs in the reaction.

The preferred examples of the reactive derivative at the terminal carboxyl group of isothiazolylthioacetic acid are an acid halide, a mixed acid anhydride, an active ester, an active amide, an acid anhydride, an acid azide, etc. When the terminal carboxyl group is a free radical, it is suitable to use a condensing agent such as N,N'-dicyclohexylcarbodiimide, N,N'-diethylcarbodiimide, etc. Also, when $R^2$ of the isothiazolylthioacetic acid is a reactive group which may hinder the reaction, such as carboxyl group, hydroxymethyl group, etc., it is preferred to use the isothiazolylthioacetic acid in the reaction after introducing a conventional protective group to the reactive group. In this case, it is preferred to release the protective group after obtaining the compound of formula IX, or after converting the compound of formula IX to the compound of formula I.

PROCESS B

The compounds of general formula IX can be also obtained by reacting a compound shown by general formula VIII and the corresponding isothiazolylthioacetic acid or the reactive derivative thereof and then reacting the product with a compound shown by general formula VII, according to Process 2.

PROCESS C

The compounds of general formula IX are further obtained by reacting the known 7α-amino-7β-haloacetamido-3-heterocyclic thiomethyl-Δ³-cephem-4-carboxylic acid shown by general formula X

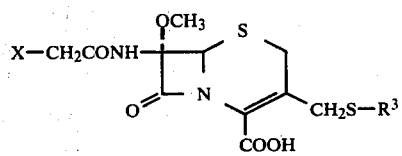

wherein $R^3$ has the same significance as above and X represents a halogen atom and a compound shown by general formula XI

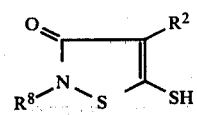

wherein $R^2$ and $R^3$ have the same significance as above and $R^8$ represents a hydrogen atom or a substituted or unsubstituted alkyl group under a basic condition.

In addition, when $R^8$ of general formula XI is a hydrogen atom, the compounds of formula XI include the tautomer thereof shown by the following formula

wherein $R^2$ has the same significance as above.

The reaction is carried out usually in a solvent at room temperature or under cooling. Any solvents which do not take part in the reaction may be used without restriction but ordinary, water, methanol, acetone, tetrahydrofuran, dimethylformamide or a mixture thereof is used as the solvent. The compounds of formula XI may be usually used as the alkali metal salt thereof at the mercapto group but when a compound of formula XI is used as it is, the reaction is carried out in the presence of an aliphatic, aromatic or heterocyclic base such as triethylamine, N,N-dimethylaniline, N-ethylmorpholine, pyridine, collidine, 2,6-lutidine, etc., or an alkali metal carbonate or alkali metal hydrogen-carbonate such as sodium carbonate, potassium carbonate, sodium hydrogencarbonate, potassium hydrogencarbonate, etc.

The compounds of general formula IX thus obtained are novel compounds. The compounds having an isothiazolylacetamide group at the 7-position have hitherto been known in the chemistry of cephalosporins as described in, for example, U.S. Pat. No. 3,464,999, but the compounds of the specific structure having an isothiazolylthioacetamide group which can be converted into a 1,3-dithietanecarboxamide group have not yet been known.

The compounds obtained by the invention exhibit excellent antibacterial activity, particularly against gram negative bacteria as shown below.

TABLE

| Example No. | Escherichia Coli NIHJ | Klebsiella pneumoniae ATCC 10031 | (M.I.C.) (γ/ml) Proteus vulgaris OXK US | Proteus morganii Kono | Seratia marcescens |
|---|---|---|---|---|---|
| 1 | 0.2 | 0.2 | 1.56 | 1.56 | 3.13 |
| 2 | 0.78 | 1.56 | 3.13 | 12.5 | 6.25 |
| 4 | 0.78 | 0.78 | 3.13 | 6.25 | 6.25 |
| 5 | 0.09 | 0.09 | 0.78 | 1.56 | 0.78 |
| 6 | 0.09 | 0.09 | 0.39 | 0.78 | 0.39 |
| 7 | 0.78 | 0.39 | 0.78 | 6.25 | 6.25 |
| 8 | 0.09 | 0.09 | 0.39 | 0.39 | 0.39 |
| 9 | 0.19 | | 0.39 | 0.78 | 0.78 |
| 11 | 0.19 | 0.19 | 1.56 | 0.39 | 0.39 |
| 12 | 0.78 | 0.39 | 0.78 | | |
| 14 | 0.19 | 0.19 | 1.56 | 1.56 | 0.78 |
| 15 | 0.19 | 0.19 | 1.56 | 3.13 | 0.78 |
| 16 | 0.39 | 0.39 | 0.78 | 6.25 | 6.25 |
| 17 | 0.39 | 0.39 | 0.78 | 0.39 | 12.5 |
| 18 | 0.78 | 0.78 | 3.13 | | |
| 19 | 0.19 | 0.09 | 0.78 | 0.39 | 1.56 |
| 22 | 0.78 | 0.39 | 0.78 | 3.13 | 3.13 |
| 23 | 1.56 | 1.56 | 1.56 | 6.25 | 6.25 |
| 24 | 0.39 | 0.39 | 0.78 | 3.13 | 0.78 |
| 25 | 0.19 | 0.09 | 0.78 | 0.39 | 0.39 |
| 26 | 0.78 | 0.39 | 1.56 | 1.56 | 0.78 |
| 29 | 0.78 | 0.78 | 1.56 | 6.25 | 1.56 |
| 30 | 0.09 | 0.20 | 0.78 | | |
| 32 | ≦0.20 | 0.20 | 0.78 | 0.78 | 0.39 |

The compounds of formula I obtained in this invention can be easily converted into the pharmaceutically acceptable, non-toxic or effective salts thereof. These salts includes the alkali metal salts such as sodium or potassium salt or salts (for example, using sodium or potassium 2-ethyl hexanoate), ammonium salt or salts, and organic amine salt or salts such as those with procaine or ethanolamine which can be prepared by one skilled in the art according to known manners.

Moreover, the pharmaceutical compositions having an actibacterial activity comprising a pharmaceutical carrier and an active but non-toxic amount of the compound of formula I as well as the methods of combatting bacterial infections by administering such a pharmaceutical composition to an infected animal or human host in an non-toxic amount sufficient to combat such infections are also the objects of this invention.

The compounds of this invention may be administered orally, rectally, or by injection such as subcutaneously, intramuscularly, or intravenously.

The injection of suitably prepared sterile solutions or suspensions containing an effective but non-toxic amount of the cephalosporin compound of this invention is the preferred route of administration.

The doses of the cephalosporin compound of the invention are usually 250-3000 mg. per day for an adult and can be variously changed according the condition of disease, the age, weight, and the state of the patient.

Then, the invention will further be described in more detail by referring to the following examples.

EXAMPLE 1

In 10 ml. of liquid ammonia was suspended 270 mg. of 4-carboxy-5-ethylthio-3-hydroxyisothiazole. After cooling the suspension to −50° C. and adding thereto 100 mg. of metallic sodium, the mixture was stirred for 30 minutes at temperatures of from −50° C. to −33° C.

Liquid ammonia was distilled off from the reaction mixture, the residue obtained was dissolved in 20 ml. of methanol, then 10 ml. of a methanol solution of 600 mg. of 7β-bromoacetamido-7α-methoxy-3-(1-methyltetrazol-5-yl)thiomethyl-Δ$^3$-cephem-4-carboxylic acid was added dropwise to the solution under ice-cooling, and after stirring the mixture for 30 minutes under ice-cooling, the mixture was further stirred for 30 minutes at room temperature. After the reaction was over, the reaction mixture was adjusted to pH 4 with 4 normal hydrochloric acid and then the reaction solvent was distilled off under reduced pressure.

To the residue formed was added water and after adjusting the mixture to pH 1 with 4 normal hydrochloric acid, the product was extracted with 50 ml. of a mixture of butanol and ethyl acetate of 1:1 by volume ratio. The organic layer formed was washed twice each time with water, then once with a saturated aqueous sodium chloride solution, dried over anhydrous magnesium sulfate, and then the solvent was distilled off under reduced pressure. To the residue was added 30 ml. of ether and the precipitates formed were recovered by filtration, washed three times each time with 20 ml. of ether, and dried under reduced pressure to provide 560 mg. of the powder of 7β-(4-carboxy-3-hydroxyisothiazol-5-yl)thioacetamido-7α-methoxy-3-(1-methyltetrazol-5-yl)thiomethyl-Δ$^3$-cephem-4-carboxylic acid.

Nuclear magnetic resonance spectra (D$_6$-DMSO) δ(p.p.m.): 3.41 (3H), 3.58 (2H), 3.93 (3H), 3.99 (2H), 4.28 (2H), 5.10 (1H).

EXAMPLE 2

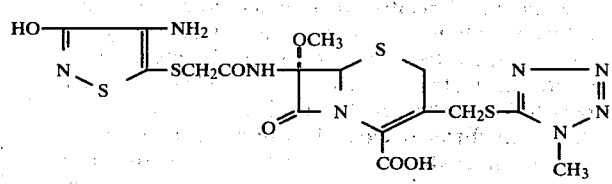

After cooling 40 ml. of liquid ammonia to −70° C., 183 mg of 4-amino-5-ethylthio-3-hydroxyisothiazole, 55 mg. of sodium was added to the liquid ammonia. The mixture was stirred for 10 minutes at the same temperature and then liquid ammonia was distilled off. To the residue was added 15 ml. of methanol followed by cooling to 2° C. The 15 ml. of a methanol solution of 300 mg. of 7β-bromoacetamido-7α-methoxy-3-(1-methyltetrazol-5-yl)thiomethyl-Δ$^3$-cephem-4-carboxylic acid was added dropwise to the mixture over a period of 30 seconds followed by stirring for 10 minutes at the same temperature. The solvent was distilled off under reduced pressure and after adding 15 ml. of water to the residue, the mixture was adjusted to pH 2.5 by adding 5% hydrochloric acid. The precipitates formed were extracted with 100 ml. of a mixture of n-butanol and ethyl acetate of 1:1 volume ratio and the extract was washed with water and then with a saturated aqueous sodium chloride solution, and dried over anhydrous magnesium sulfate. The solvent was distilled off and the residue formed was subjected to a silica gel column chromatography to provide 180 mg. of 7β-(4-amino-3-hydroxyisothiazol-5-yl)thioacetamido-7β-methoxy-3-(1-methyltetrazol-5-yl)thiomethyl-Δ³-cephem-4-carboxylic acid using a mixture of chloroform, methanol, and formic acid of 8:2:0.2 by volume ratio as the eluant.

Nuclear magnetic resonance spectra (D₆-DMSO)
δ(p.p.m.): 3.36 (3H), 3.54 (2H), 3.58 (2H), 3.94 (2H), 4.30 (2H), 5.09 (1H).

EXAMPLE 3

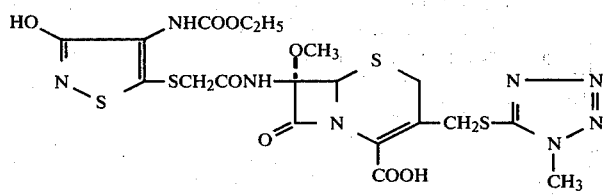

By following the same procedure as in Example 2, 50 mg. of 7β-(4-ethoxycarbonylamino-3-hydroxyisothiazol-5-yl)thioacetamido-7α-methoxy-3-(1-methyltetrazol-5-yl)thiomethyl-Δ³-cephem-4-carboxylic acid was obtained from 300 mg. of 4-ethoxycarbonylamino-5-ethylthio-3-hydroxyisothiazole and 300 mg. of 7β-bromoacetamido-7α-methoxy-3-(1-methyltetrazol-5-yl)thiomethyl-Δ³-cephem-4-carboxylic acid.

Nuclear magnetic resonance spectra (D₆-DMSO)
δ(p.p.m.): 1.14 (3H), 3.38 (3H), 3.60 (2H), 3.81 (2H), 3.92 (3H), 4.06 (2H), 4.29 (2H), 5.11 (1H).

EXAMPLE 4

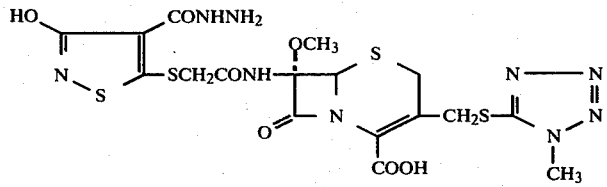

By following the same procedure as in Example 2, 100 mg. of 7β-(4-carbazoyl-3-hydroxyisothiazol-5-yl)thioacetamido-7α-methoxy-3-(1-methyltetrazol-5-yl)thiomethyl-Δ³-cephem-4-carboxylic acid was obtained from 220 mg. of 4-carbazoyl-5-ethylthio-3-hydroxyisothiazole and 400 mg. of 7β-bromoacetamido-7α-methoxy-3-(1-methyltetrazol-5-yl)thiomethyl-Δ³-cephem-4-carboxylic acid.

Nuclear magnetic resonance spectra (D₆-DMSO)
δ(p.p.m.): 3.39 (3H), 3.63 (2H), 3.90 (2H), 3.93 (3H), 4.30 (2H), 5.13 (1H).

EXAMPLE 5

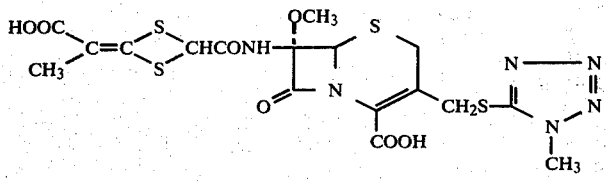

(a) In 15 ml. of methylene chloride were dissolved 0.340 g. of 4-[1-(tert-butoxycarbonyl)ethylidene]-1,3-dithietane-2-carboxylic acid and 0.206 g. of pyridine. The while stirring the solution in an ice-water bath, 0.284 g. of phosphorus pentachloride was added to the solution. The reaction was carried out for one hour at temperature below 10° C. and then after cooling the reaction mixture to −50° C., a solution of 0.690 g. of 7β-amino-7α-methoxy-3-(1-methyltetrazol-5-yl)thiomethyl-Δ³-cephem-4-carboxylic acid benzhydryl ester in 10 ml. of methylene chloride was added dropwise to the solution and then 1.6 ml. of pyridine was added dropwise and the mixture was reacted for one hour at temperatures of from −30° C. to −40° C.

After the reaction was over, 10 ml. of 5 normal hydrochloric acid was added dropwise to the reaction mixture below 0° C. and the product was extracted with methylene chloride. The extract was washed with a saturated aqueous sodium chloride solution, dried over anhydrous calcium chloride, and then methylene chloride was distilled off to provide 1.1 g. of a residue. The residue was subjected to a silica gel column chromatography and then 0.490 g. (yield 47%) of caramel-like 7β-{4-[1-(tert-butoxycarbonyl)ethylidene]-1,3-dithietan-2-yl}carboxamido-7α-methoxy-3-(1-methyltetrazol-5-yl)thiomethyl-Δ³-cephem-4-carboxylic acid benzhydryl ester was obtained using a mixture of ethyl acetate and n-hexane of 1:1 by volume ratio as the eluant.

Nuclear magnetic resonance spectra (D₆-DMSO)

δ(p.p.m.): 1.44 (9H, tert-butyl), 1.56 (3H, $\overset{-OOC}{\underset{CH_3}{>}}=$), 3.49 (3H, OCH₃), -continued 3.90 (3H, 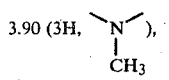), 5.10 (1H)  
5.15 (1H)  } H of C$_6$ and 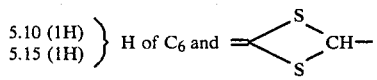

6.92 (1H, —CH(C$_6$H$_5$)$_2$), 9.68 (1H, —CONH—).

(b) In 25 ml. of anisole was dissolved 0.44 g. of the product obtained in step (a) and while cooling the solution below 5° C. with ice-water, 7.5 ml. of trifluoroacetic acid was added dropwise to the solution. The reaction was performed for one hour at 5°–10° C., anisole and excess trifluoroacetic acid were distilled off under reduced pressure, and the residue was powdered by adding thereto ether. After recovering the powder by filtration, the powder was washed well with ether to provide 0.271 g. (yield 86.7%) of the light yellow powder of 7β-[4-(1-carboxyethylidene)-1,3-dithietan-2-yl]carboxamido-7α-methoxy-3-(1-methyltetrazol-5-yl)thiomethyl-Δ$^3$-cephem-4-carboxylic acid.

Nuclear magnetic resonance spectra (D$_6$-DMSO)

δ(p.p.m.): 1.56 (3H, 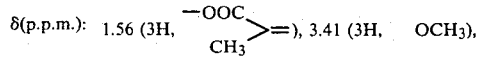), 3.41 (3H, OCH$_3$), 3.93 (3H, 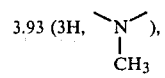), 5.13 (2H, H of C$_6$ and 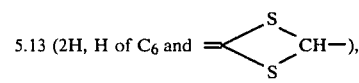), 9.57 (1H, —CONH—)

Infrared spectrum (KBr) (cm$^{-1}$) 1870 (lactam).

Reference example 1

In a 100 ml. three-necked flask were placed 40 ml. of dimethoxyethane and 10 ml. of tetrahydrofuran both were deoxygenated by distillation. While cooling the mixture below −70° C. by a dry ice acetone bath in nitrogen stream, 1 ml. of n-isopropylcyclohexylamine and 3.43 ml. of a 15% n-butyl lithium n-hexane solution were added to the mixture. Then, after adding thereto 0.65 g. of tert-butyl propionate, the reaction was carried out for about 30 minutes at temperature below −70° C. with stirring. To the reaction mixture was added dropwise 0.332 ml. of carbon disulfide at temperatures of from −75° C. to −73° C. over a period of about 30 minutes. The reaction was further carried out for 10 minutes at temperature below −70° C. and then 3.4 ml. of a 15% n-butyl lithium n-hexane solution was added dropwise to the reaction mixture at temperature below −70° C. over a period of about 30 minutes. After carrying out the reaction for 15 minutes at temperature below −70° C., sodium diiodoacetate obtained beforehand by reacting 0.24 g. of 50% oily sodium hydride and 1.56 g. of diiodoacetic acid in 10 ml. of dimethoxyethane under ice-cooling, was added to the reaction mixture and the mixture was stirred overnight at room temperature.

The solvent was distilled off from the reaction mixture under reduced pressure and after adding cold ether to the residue and acidifying the residue with 1 normal hydrochloric acid, the product was extracted with ether. The ether extract was washed well with a saturated aqueous sodium chloride solution, dried over anhydrous magnesium sulfate, and then ether was distilled off to provide 1.42 g. of a brown oily product. The product was subjected to silica gel column chromatography and 0.5 g. of oily 4-[1-(tert-butoxycarbonyl)-ethylidene]-1,3-dithietane-2-carboxylic acid was obtained using a mixture of chloroform, methanol, and formic acid of 95:5:2 by volume ratio as the eluant.

Nuclear magnetic resonance spectra (D$_6$-DMSO)

δ(p.p.m.): 1.42 (9H, tert-butyl)

1.53 (3H, 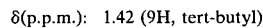)

5.14 (1H, 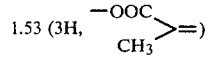)

Infrared spectra (cm$^{-1}$): 2970 (tert-butyl), 2520-2650 (-COOH), 1640-1740 (-COO-tert-butyl, -COOH), 1360, 1250, and 840 (tert-butyl)

EXAMPLE 6

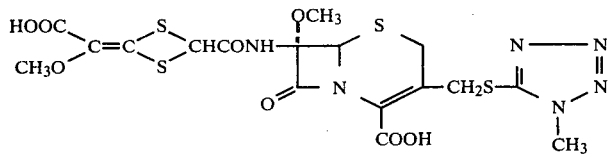

(a) In 5 ml. of tetrahydrofuran were dissolved 0.7 g. of 7β-amino-7α-methoxy-3-(1-methyltetrazol-5-yl)thiomethyl-Δ$^3$-cephem-4-carboxylic acid benzhydryl ester and 0.35 g. of 4-[(tert-butoxycarbonyl)(methoxy)methylene]-1,3-dithietane-2-carboxylic acid and after adding thereto 0.3 g. of N,N'-dicyclohexylcarbodiimide under ice-cooling, the mixture was stirred for two hours at room temperature. Insoluble materials were filtered off and the filtrate was concentrated under reduced pressure. The residue was subjected to a column chromatography and 0.36 g. of 7β-{4-[(tert-butoxycarbonyl)(methoxy)-methylene]-1,3-dithietan-2-yl}carboxamido-7α-methoxy-3-(1-methyltetrazol-5-yl)thiomethyl-Δ$^3$-cephem-4-carboxylic acid benzhydryl ester was obtained using a mixture of benzene and ethyl acetate of 85:15 by volume ratio as the eluant.

Nuclear magnetic resonance spectra (CDCl$_3$)

δ(p.p.m.): 1.50 (9H, tert-butyl)

3.59 (3H)  
3.64 (3H)  } OCH$_3$ of C$_7$ and 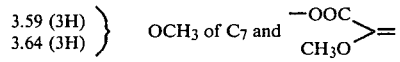

3.82 (3H, 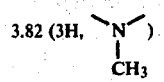)

4.38 (2H, —CH₂S— of C₃), 4.77 (1H, 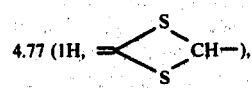), 5.07 (1H, H of C₆), 6.92 (1H, —CH(C₆H₅)₂), 7.2–7.5 (10H, —CH(C₆H₅)₂)

(b) In 1.7 ml. of anisole was dissolved 0.23 g. of the product obtained in step (a) and while cooling the solution to temperature of from −5° C. to −10° C., 5.1 ml. of trifluoroacetic acid was added gradually followed by stirring for 30 minutes at 0°–8° C.

The reaction mixture was concentrated under reduced pressure, ether was added to the residue, and the faint brown powder formed was recovered by filtration. The powder was washed well with ether and dried under reduced pressure to provide 0.12 g. of 7β-{4-[(carboxy)(methoxy)methylene]-1,3-dithietan-2-yl}carboxamido-7α-methoxy-3-(1-methyltetrazol-5-yl)thiomethyl-Δ³-cephem-4-carboxylic acid.

Nuclear magnetic resoance spectra (D₆-DMSO)

δ(p.p.m.): 3.42 (3H, OCH₃ of C₇)

3.55 (3H, 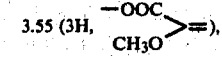), 3.85 (3H, 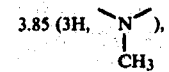), 5.16 (2H, H of C₆ and 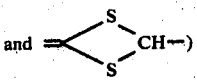)

9.59 (1H, —CONH—).

Reference example 2:

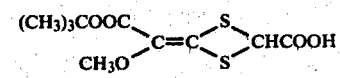

A mixture of 4.5 g. of tert-butyl methoxyacetate and 10 ml. of tetrahydrofuran was added to a lithium diisopropylamine solution prepared by adding 18.2 ml. of a 15% n-butyl lithium hexane solution to a mixture of 3 g. of diisopropylamine and 20 ml. of tetrahydrofuran at temperature of from −40° C. to −70° C. and then after adding thereto 0.9 ml. of carbon disulfide at temperature below −40° C., the resultant mixture was stirred for 20 minutes at the same temperature. Then, after adding to the resulting reaction mixture the lithium diisopropylamine solution of ½ of the aforesaid amount and carbon disulfide of ½ of the aforesaid amount at temperature of from −40° C. to −70° C. to cause reaction, the lithium diisopropylamine solution of ¼ of the aforesaid amount and carbon disulfide of ¼ of the aforesaid amount were further added to the mixture to cause reaction. Then 9 g. of sodium diiodoacetate was added to the reaction mixture followed by rising gradually the temperature and stirring for one hour at 0°–5° C. and further for one hour at room temperature. The reaction mixture obtained was concentrated under reduced pressure and after adding 20 ml. of 10% hydrochloric acid to the residue formed, the product was extracted with 100 ml. of benzene. The extract was washed with water and concentrated under reduced pressure. The residue formed was subjected to a silica gel column chromatography and 5.6 g. of 4-[(tert-butoxycarbonyl)(methoxy)methylene]-1,3-dithietane-2-carboxylic acid was obtained using a mixture of chloroform and ethanol of 10:2.5 by volume ratio as the eluant.

Nuclear magnetic resonance spectra (CDCl₃)

δ(p.p.m.): 1.52 (9H, (CH₃)₃COOC—), 3.67 (3H, CH₃O—), 4.88 (1H, 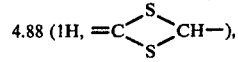), 8.64 (1H, —COOH).

EXAMPLE 7

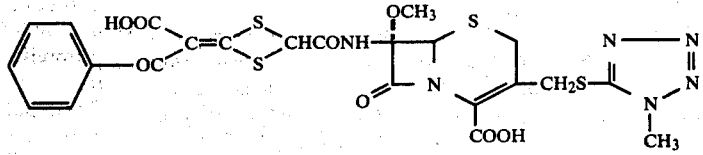

(a) By treating 0.8 g. of 7β-amino-7α-methoxy-3-(1-methyltetrazol-5-yl)thiomethyl-Δ³-cephem-4-carboxylic acid benzhydryl ester and 0.8 g. of 4-[(benzoyl)(tert-butoxycarbonyl)-methylene]-1,3-dithietane-2-carboxylic acid as in Example 6-(a), 0.35 g. of 7β-{4-[(benzoyl)(tert-butoxycarbonyl)methylene]-1,3-dithietan-2-yl}carboxamido-7α-methoxy-3-(1-methyltetrazol-5-yl)thiomethyl-Δ³-cephem-4-carboxylic acid benzhydryl ester was obtained.

Nuclear magnetic resonance spectra (CDCl₃)

δ(p.p.m.): 1.24 (9H, tert-butyl), 3.60 (3H, OCH₃), 3.82 (3H, 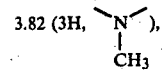), 4.39 (2H, —CH₂S— of C₃), 5.00 (1H)  
5.09 (1H) } H of C₆ and 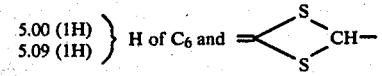

6.92 (1H, —CH(C₆H₅)₂), 7.2–7.6 (15H, H of aromatic ring), 7.77 (1H, —CONH—).

(b) By treating 0.23 g. of the product obtained in step (a) as in Example 6-(b), 0.13 g. of 7β-{4-[(benzoyl)(carboxy)methylene]-1,3-dithietan-2-yl}carboxamido-7α-methoxy-3-(1-methyltetrazol-5-yl)thiomethyl-Δ³-cephem-4-carboxylic acid was obtained.

Nuclear magnetic resonance spectra (D₆-DMSO)

(p.p.m.): 3.46 (3H, OCH₃),

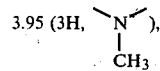

3.95 (3H, ), 
   |
   CH₃

4.32 (2H, —CH₂— of C₂), 5.19 (1H, H of C₆),

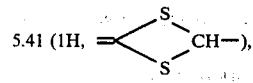

5.41 (1H, CH—), 7.48 (5H, C₆H₅—OC—), 9.72 (1H, —CONH—).

Reference example 3:

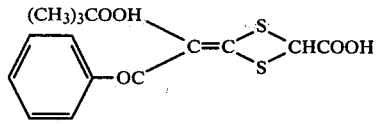

In a mixture of 2.2 g. of tert-butyl benzoylacetate and 20 ml. of tert-butanol was dissolved 0.24 g. of sodium hydride (50% in oil), and 0.6 ml. of carbon disulfide was added to the solution at 15°–20° C. followed by stirring for 40 minutes, 0.24 g. of sodium hydride (50% in oil) was then added to the mixture followed by stirring for one hour. To the reaction mixture obtained was added 1.52 g. of sodium dichloroacetate followed by stirring for 4 hours at room temperature. The reaction mixture was concentrated under reduced pressure and after adding 30 ml. of 1 normal hydrochloric acid to the residue formed, the product was extracted with 30 ml. of benzene. The extract was washed with water, dried, and concentrated under reduced pressure. By adding a mixture of benzene and n-hexane of 3:1 by volume ratio to the residue formed, 0.9 g. of the yellowish crystals of 4-[(benzoyl)(tert-butoxycarbonyl)methylene]-1,3-dithietane-2-carboxylic acid were obtained.

EXAMPLE 8

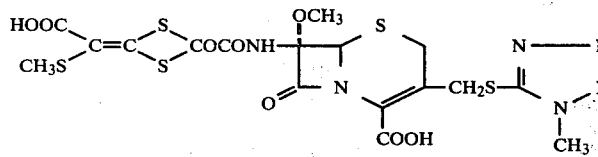

(a) In 10 ml. of anhydrous tetrahydrofuran were dissolved 0.3 g. of 4-[(tert-butoxycarbonyl)(methylthio)methylene]-1,3-dithietane-2-carboxylic acid, 0.2 g. of N,N'-dicyclohexylcarbodiimide, and 0.5 g. of 7β-amino-7α-methoxy-3-(1-methyltetrazol-5-yl)-thiomethyl-Δ³-cephem-4-carboxylic acid benzhydryl ester. Then the solution was stirred for one hour at room temperature. The solvent was distilled off under reduced pressure. The residue formed was subjected to a silica gel column chromatography and 0.3 g. of 7β-{4-[(tert-butoxycarbonyl)-(methylthio)methylene]-1,3-dithietan-2-yl}carboxamido-7α-methoxy-3-(1-methyltetrazol-5-yl)thiomethyl-Δ³-cephem-4-carboxylic acid benzhydryl ester was obtained using a mixture of benzene and ethyl acetate of 9:1 by volume ratio as the eluant.

Nuclear magnetic resonance spectra (CDCl₃)

δ(p.p.m.): 1.52 (9H, tert-butyl), 2.22 (3H, CH₃S—), 3.78 (5H, OCH₃ and —CH₂— of C₂), 3.82 (3H, ),
   |
   CH₃

4.24 (2H, —CH₂S— of C₃), 4.72 (1H, CH—), 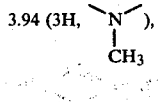

5.08 (1H, H of C₆), 6.92 (1H, —CH(C₆H₅)₂), 7.35 (10H, —CH(C₆H₅)₂), 7.80 (1H, —CONH—).

(b) In 1.5 ml. of anisole was dissolved 0.3 g. of the product obtained in step (a) and while stirring the solution at −5° C., 5 ml. of trifluoroacetic acid was added dropwise to the solution at temperature of from −5° C. to −3° C. followed by stirring for one hour at 0°–3° C. The reaction mixture was evaporated to dryness under reduced pressure and ether was added to the residue formed. The precipitates were recovered by filtration and washed well with ether and dried over phosphorus pentoxide under reduced pressure to provide 0.17 g. of 7β-{4-[(carboxy)(methylthio)-methylene]-1,3-dithietan-2-yl}carboxamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 1.16 (3H, CH₃S—), 3.43 (3H, OCH₃), 3.62 (2H, —CH₂— of C₂), 3.94 (3H, ),
   |
   CH₃

4.30 (—CH₂S— of C₃), 5.09 (1H, H of C₆), 5.16 (1H, =C(S)(S)CH—), 9.65 (1H, —CONH—).

Reference example 4:

(CH₃)₃COOC\C=C/S\CHCOOH
      CH₃S/   \S/

In 14 ml. of anhydrous tetrahydrofuran was suspended 0.96 g. of sodium hydride (50% in oil). After adding dropwise a mixture of 20 ml. of tert-butanol and 15 ml. of anhydrous tetrahydrofuran to the suspension, the mixture was stirred for 10 minutes at room temperature. Then, to the mixture was added a mixture of 1.62 g. of tert-butyl methylthioacetate and 5 ml. of anhydrous tetrahydrofuran at 3°–5° C. and after 30 minutes, 0.6 ml. of carbon disulfide was added to the mixture at the same temperature followed by stirring for 50 minutes. Then, 3.34 g. of sodium diiodoacetate was added to the mixture at temperature below 7° C. and they were caused to react for 50 minutes under ice-cooling. The solvent was distilled off under reduced pressure, the residue formed was dissolved in 50 ml. of ice-water, and the solution was washed twice each with ether. The aqueous layer formed was recovered, adjusted to pH 2 with 10% hydrochloric acid, dried over anhydrous magnesium sulfate, and then ether was distilled off under reduced pressure. The residue was subjected to a silica gel column chromatography and 1.3 g. of oily 4-[(tert-butoxycarbonyl)(methylthio)methylene]-1,3-dithiethane-2-carboxylic acid using a mixture of chloroform, methanol, and formic acid of 95:5:2 by volume ratio as the eluant.

Nuclear magnetic resonance spectra (CDCl₃)

δ(p.p.m.): 1.52 (9H, (CH₃)₃COOC—), 2.22 (3H, CH₃S—), 4.74 (1H, =C(S)(S)CH—), 9.12 (1H, —COOH).

EXAMPLE 9

HOOC\C=C/S\CHCONH—[β-lactam structure]—CH₂S—[tetrazole]
CH₃CH₂S/   \S/

(a) By treating 0.15 g. of 4-[(tert-butoxycarbonyl)-(ethylthio)methylene]-1,3-dithietane-2-carboxylic acid, 0.1 g. of N,N'-dicyclohexylcarbodiimide, and 0.26 g. of 7β-amino-7α-methoxy-3-(1-methyltetrazol-5-yl)thiomethyl-Δ³-cephem-4-carboxylic acid benzhydryl ester as in Example 8-(a), 0.14 g. of 7β-{4-[(tert-butoxycarbonyl)(ethylthio)methylene]-1,3-dithietan-2-yl}carboxamido-7α-methoxy-3-(1-methyltetrazol-5-yl)thiomethyl-Δ³-cephem-4-carboxylic acid benzhydryl ester was obtained.

Nuclear magnetic resonance spectra (CDCl₃)

δ(p.p.m.): 1.22 (3H, CH₃CH₂S—), 1.52 (9H, tert-butyl), 2.68 (2H, CH₃CH₂S—), 3.58 (5H, —CH₂— of C₂ and OCH₃), 38.2 (3H OCH₃), 4.38 (2H, —CH₂— of C₂), 4.70 (1H, =C(S)(S)CH—), 5.08 (1H, H of C₆), 6.92 (1H, —CH(C₆H₅)₂), 7.32 (10H, —CH(C₆H₅)₂), 7.79 (1H, —CONH—).

(b) By treating a mixture of 0.14 g. of the product obtained in step (a), 1.5 ml. of anisole, and 5 ml. of trifluoroacetic acid as in Example 8-(b), 0.07 g. of 7β-{4-[(carboxy)-(ethylthio)methylene]-1,3-dithietan-2-yl}carboxamido-7α-methoxy-3-(1-methyltetrazol-5-yl)thiomethyl-Δ³-cephem-4-carboxylic acid was obtained.

Nuclear magnetic resonance spectra (D₆-DMSO)

δ(p.p.m.): 1.14 (3H, CH₃CH₂S—), 2.62 (2H, CH₃CH₂S—), 3.43 (3H, OCH₃), 3.61 (2H, —CH₂— of C₂), 3.94 (3H, N—CH₃), 4.28 (2H, —CH₂S— of C₃), 5.08 (1H, H of C₆), 5.14 (1H, =C(S)(S)CH—), 9.64 (1H, —CONH—).

Reference example 5:

(CH₃)₃COOC\C=C/S\CHCOOH
CH₃CH₂S/   \S/

By treating 3.4 g. of tert-butyl ethylthioacetate as in Reference example 4, 4.05 g. of oily 4-[(tert-butoxycarbonyl)-(ethylthio)methylene]-1,3-dithietane-2-carboxylic acid was obtained.

Nuclear magnetic resonance spectra (CDCl₃)

δ(p.p.m.): 1.42 (3H, CH₃CH₂S—), 1.52 (9H, (CH₃)₃COOC—), 2.68 (2H, CH₃CH₂S—), 4.76 (1H, =C(S)(S)CH—), 9.52 (1H, —COOH).

EXAMPLE 10

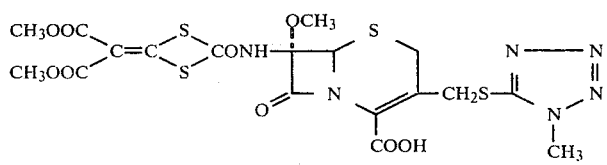

In 5 ml. of methylene chloride was dissolved 400 mg. of 4-[bis(methoxycarbonyl)methylene]-1,3-dithietane-2-carboxylic acid. After adding thereto 180 mg. of pyridine and further 290 mg. of phosphorus pentachloride under ice-cooling, the mixture was stirred for 30 minutes. The solution was added to a solution prepared by dissolving 500 mg. of 7β-amino-7α-methoxy-3-(1-methyltetrazol-5-yl)thiomethyl-Δ³-cephem-4-carboxylic acid benzhydryl ester in 10 ml. of methylene chloride and cooling the solution to −20° C. to −30° C. The mixture was then stirred for one hour at the same temperature. The reaction mixture was washed successively with 10 ml. of water, 5 ml. of diluted hydrochloric acid, and 5 ml. of water, then dried over anhydrous magnesium sulfate, and distilled under reduced pressure. The residue was subjected to a silica gel column chromatography to provide 450 mg. of 7β-[4-{bis(methoxycarbonyl)methylene}-1,3-dithietan-2-yl]-carboxamido-7α-methoxy-3-(1-methyltetrazol-5-yl)thiomethyl-Δ³-cephem-4-carboxylic acid benzhydryl ester using a mixture of chloroform and ethyl acetate of 6:1 by volume ratio as the eluant.

Nuclear magnetic resonance spectra (CDCl₃)

δ(p.p.m.): 3.58 (5H, CH₃O— of C₇ and —CH₂— of C₂), 3.80 (6H, —COOCH₃), 3.83 (3H, N-methyltetrazole), 4.20 (2H, —CH₂S— of C₃), 4.84 (1H, =C(S)(S)CH—), 5.07 (1H, H of C₆), 6.93 (1H, —CH(C₆H₅)₂), 7.36 (10H, H of phenyl of —CH(C₆H₅)₂).

In a mixture of 4 ml. of trifluoroacetic acid and 1 ml. of anisole was dissolved 400 mg. of 7β-[4-{bis(methoxycarbonyl)methylene}-1,3-dithietan-2-yl]carboxamido-7α-methoxy-3-(1-methyltetrazol-5-yl)thiomethyl-Δ³-cephem-4-carboxylic acid benzhydryl ester. The solution was stirred for one hour under ice-cooling. The reaction mixture was evaporated to dryness and the residue was mixed with ether. The product was recovered by filtration, washed well with ether, and dried overnight over phosphorus pentoxide under reduced pressure to provide 200 mg. of 7β-[4-{bis(methoxycarbonyl)methylene}-1,3-dithietan-2-yl]carboxamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 3.44 (3H, CH₃O— of C₇), 3.70 (6H, —COOCH₃), 3.93 (3H, N-methyltetrazole), 4.29 (2H, —CH₂S— of C₃), 5.08 (1H) } =C(S)(S)CH— and H of C₆
5.16 (1H) }

Reference example 6

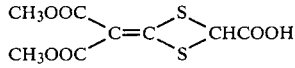

In 10 ml. of anhydrous tetrahydrofuran was suspended 2.1 g. of disodium 2,2-bis(methoxycarbonyl)ethylene-1,1-dithiolate.

After adding 2.2 g. of sodium dibromoacetate to the suspension, the mixture was stirred for 2 hours at room temperature. The solvent was distilled off from the reaction mixture under reduced pressure and the residue was dissolved in 5 ml. of water. The solution was adjusted to pH 3.5–4.0 with diluted hydrochloric acid and extracted with ethyl acetate. The extract was dried over anhydrous magnesium sulfate and the solvent was distilled off under reduced pressure. The residue was mixed with ether and filtered to provide 1.5 g. of 4-[bis(methoxycarbonyl)methylene]-1,3-dithietane-2-carboxylic acid. Nuclear magnetic resonance spectra (D₆-DMSO)

δ(p.p.m.): 3.70 (6H, (CH₃OOC)₂C=), 5.20 (1H, =C(S)(S)CH—)

EXAMPLE 11

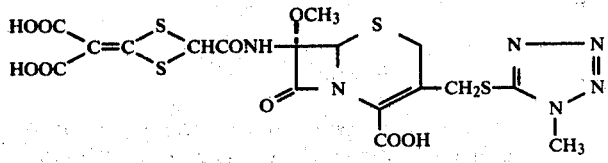

(a) In 5 ml. of methylene chloride was dissolved 500 mg. of [4-bis(tert-butoxycarbonyl)methylene-1,3-dithietan-2-yl]carboxylic acid. Then after adding 226 mg. of pyridine and further 360 mg. of phosphorus pentachloride to the solution under ice-cooling, the mixture was stirred for 30 minutes. The mixture was added to a solution prepared by dissolving 500 mg. of 7β-amino-7α-methoxy-3-(1-methyltetrazol-5-yl)-thiomethyl-Δ³-cephem-4-carboxylic acid benzhydryl ester in 10 ml. methylene chloride and cooling to a temperature of from −20° C. to −30° C. and the mixture was stirred for one hour at the same temperature. The reaction mixture was washed successively with 10 ml. of water, 5 ml. of diluted hydrochloric acid, and 5 ml. of water, dried over anhydrous magnesium sulfate, and then the solvent was distilled off under reduced pressure. The residue was subjected to a silica gel column chromatography using a mixture of chloroform and ethyl acetate of 6:1 by volume ratio as the eluant to provide 300 mg. of 7β-[4-{bis(tert-butoxycarbonyl)methylene}-1,3-dithietan-2-yl]carboxamido-7α-methoxy-3-(1-methyltetrazol-5-yl)thiomethyl-Δ³-cephem-4-carboxylic acid benzhydryl ester.

Nuclear magnetic resonance spectra (CDCl₃)

δ(p.p.m.):  1.50 (18H, t-C₄H₉), 3.60 (5H, CH₃O— C₇ and —CH₂— of C₂), 3.86 (3H, 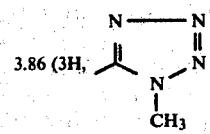

4.40 (2H, —CH₂—S— of C₃), 4.82 (1H, 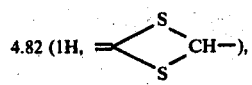 ), 5.10 (1H, H of C₆), 6.94 (1H, —CH(C₆H₅)₂), 7.38 (10H, H of the phenyl of —CH(C₆H₅)₂).

(b) In a mixture of 4 ml. of trifluoroacetic acid and 0.5 ml. of anisole was dissolved 200 mg. of 7β-[4-{bis(tert-butoxycarbonyl)methylene}-1,3-dithietan-2-yl]carboxamido-7α-methoxy-3-(1-methyltetrazol-5-yl)thiomethyl-Δ³-cephem-4-carboxylic acid benzhydryl ester. The solution was stirred for one hour under ice-cooling. Then, the solvents were distilled off under reduced pressure and ether was added to the residue formed to form precipitates which were recovered by filtration. By washing the precipitates with ether, 100 mg. of 7β-{4-(dicarboxymethylene)-1,3-dithietan-2-yl}-carboxamido-7α-methoxy-3-(1-methyltetrazol-5-yl)thiomethyl-Δ³-cephem-4-carboxylic acid was obtained.

Nuclear magnetic resonance spectra (D₆-DMSO)

δ(p.p.m.):  3.44 (3H, CH₃O— of C₇), 3.64 (2H, —CH₂— of C₂), 3.93 (3H, 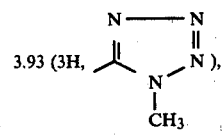 ), 4.30 (2H, —CH₂—S— of C₃), 5.16 (1H)
5.24 (1H)  H of C₆ and 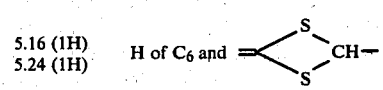

Reference example 7:

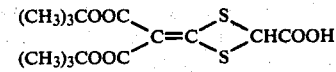

By following the same procedure as in Reference example 6 using disodium 2,2-bis(tert-butoxycarbonyl)ethylene-1,1-dithiolate, 4-[bis(tert-butoxycarbonyl)methylene]-1,3-dithietane-2-carboxylic acid was obtained.

Nuclear magnetic resonance spectra (D₆-DMSO)

δ(p.p.m.):  1.46 (9H, (CH₃)₃COOC—), 5.18 (1H, 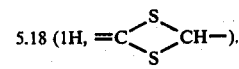 ).

EXAMPLE 12

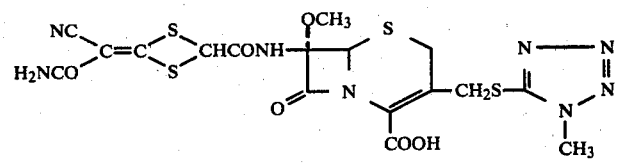

(a) In 12 ml. of tetrahydrofuran were dissolved 370 mg. of 7β-amino-7α-methoxy-3-(1-methyltetrazol-5-yl)thiomethyl-Δ³-cephem-4-carboxylic acid benzhydryl ester, 150 mg. of N,N'-dicyclohexylcarbodiimide, and 150 mg. of 4-[(carbamoyl)(cyano)-methylene]-1,3-dithietane-2-carboxylic acid followed by stirring for 2 hours at room temperature. The precipitates which had formed were filtered off and the solvent was distilled off from the filtrate under reduced pressure. The residue was subjected to a silica gel column chromatography using a mixture of chloroform and iso-propanol of 9:1 by volume ratio as the eluant to provide 190 mg. of 7β-[4-{(carbamoyl)(cyano)-methylene}-1,3-dithietan-2-ylcarboxamido]-7α-methoxy-3-(1-methyltetrazol-5-yl)thiomethyl-Δ³-cephem-4-carboxylic acid benzhydryl ester.

Nuclear magnetic resonance spectra (CDCl₃)

δ(p.p.m.): 3.55 (3H, 2H, CH₃O and —CH₂— of C₂), 3.83 (3H, CH₃—N⟨⟩),

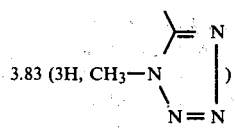

4.32 (2H, —CH₂— of C₃), 5.08 (1H)  
5.20 (1H) } H of C₆ and =C⟨S⟩⟨S⟩CHCO—

6.92 (1H, φ₂CH—), 7.30 (10H, (C₆H₅)₂CH—).

(b) In 10 ml. of methylene chloride was dissolved 160 mg. of the product obtained in above step (a). After adding thereto 0.5 ml. of anisole, the mixture was cooled to −20° C. Then, after adding dropwise 25 ml. of trifluoroacetic acid to the mixture at a temperature of from −20° C. to −10° C., the mixture was stirred for one hour at −10° C. to 0° C. The solvent was distilled off under reduced pressure and after adding 15 ml. of ether to the residue formed, the mixture was stirred for 20 minutes. Then, the mixture was filtered under reduced pressure and the precipitates thus obtained were washed well with ether and dried under reduced pressure to provide 80 mg. of 7β-[4-{(carbamoyl)(cyano)-methylene}-1,3-dithietan-2-ylcarboxamido]-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 3.44 (3H, CH₃O—), 3.84 (2H, —CH₂— of C₂), 3.95 (3H, CH₃—N⟨⟩), 4.32 (2H, —CH₂— of C₃), 5.17 (1H, H of C₆), 5.51 (1H, =C⟨S⟩⟨S⟩CHCO—).

Reference example 8:

-continued

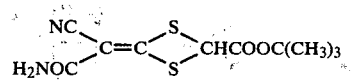

In 50 ml. of dimethyl sulfoxide was dissolved 4.8 g. of disodium 2-carbamoyl-2-cyano-ethylene-1,1-dithiolate. After adding 6.28 g. of tert-butyl dibromoacetate to the solution, the mixture was stirred for 48 hours at room temperature. The solvent was distilled off from the reaction mixture obtained under reduced pressure and the product was extracted with ethyl acetate. The extract was washed with water and then an aqueous sodium chloride solution, dried over anhydrous magnesium sulfate, and then the solvent was distilled off under reduced pressure. The residue was subjected to a silica gel column chromatography and 0.8 g. of tert-butyl 4-[(carbamoyl)(cyano)methylene]-1,3-dithietane-2-carboxylate using a mixture of chloroform and ethyl acetate of 7:1 by volume ratio as the eluant.

Nuclear magnetic resonance spectra (D₆-DMSO)

δ(p.p.m.): 1.47 (9H, (CH₃)₃COOC—), 5.42 (1H, =C⟨S⟩⟨S⟩CH—),

Reference example 9:

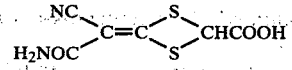

To 0.4 g. of tert-butyl 4-[(carbamoyl)(cyano)methylene]-1,3-dithietan-2-carboxylate obtained in Reference example 7 were added 2 ml. of anisole and 8 ml. of trifluoroacetic acid. The mixture was then stirred for one hour at room temperature. The solvents were distilled off under reduced pressure and the residue was mixed with 10 ml. of ether followed by stirring for one hour. The precipitates thus formed were recovered by filtration, washed with ether, and dried under reduced pressure to provide 0.15 g. of 4-[(carbamoyl)(cyano)methylene]-1,3-dithietane-2-carboxylic acid.

EXAMPLE 13

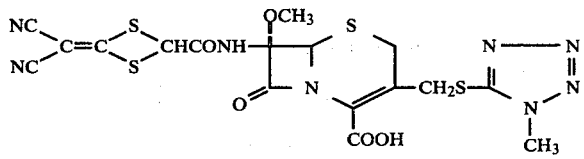

(a) In 12 ml. of methylene chloride was dissolved 0.43 g. of 7β-amino-7α-methoxy-3-(1-methyltetrazol-5-yl)thiomethyl-Δ³-cephem-4-carboxylic acid benzhydryl ester. After cooling the solution to −40° C., 0.65 g. of pyridine was added thereto. Then, a solution prepared by dissolving 0.2 g. of 4-(dicyanomethylene)-1,3-dithietane-2-carboxylic acid in 8 ml. of methylene chloride, adding 0.21 g. of phosphorus pentachloride, and stirring the mixture for 25 minutes at room temperature was added dropwise to the above-prepared mixture at a temperature of from −40° C. to −25° C. and then the mixture was stirred for one hour at −30° C. to −20° C. After the reaction was over, 60 ml. of chloroform was added to the reaction mixture and the mixture was washed with 1% hydrochloric acid, water, and then a saturated aqueous sodium chloride solution. The organic layer formed was recovered and dried over anhydrous magnesium sulfate. The solvents were distilled off under reduced pressure and the residue was subjected to a silica gel column chromatography to provide 0.37 g. of 7β-[4-(dicyanomethylene)-1,3-dithietan-2-yl]-carboxamido-7α-methoxy-3-(1-methyltetrazol-5-yl)thiomethyl-Δ³-cephem-4-carboxylic acid benzhydryl ester using a mixture of chloroform and iso-propanol of 40:1 by volume ratio as the eluant.

Nuclear magnetic resonance spectra (CDCl₃)

δ(p.p.m.): 3.54 (5H, —CH₂— of C₂ and OCH₃), 3.86 (3H, 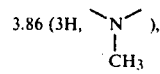), 4.30 (2H, —CH₂S— of C₃), 5.06 (2H, H of C₆ and 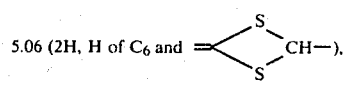), 6.90 (1H, —CH(C₆H₅)₂)

7.30 (10H, —CH(C₆H₅)₂).

(b) In 10 ml. of methylene chloride was dissolved 0.37 g. of the product obtained in above step (a). After adding 0.5 ml. of anisole to the solution, the mixture was cooled to −20° C. Then, 2 ml. of trifluoroacetic acid was added dropwise to the mixture at −20° C. to −10° C. and the resultant mixture was stirred for 30 minutes at −10° C. to −5° C. The solvent was distilled off under reduced pressure and 20 ml. of ether was added to the residue followed by stirring for 30 minutes. The mixture was filtered under reduced pressure and the precipitates obtained were washed well with ether and dried under reduced pressure to provide 0.21 g. of 7β-[4-(dicyanomethylene)-1,3-dithietan-2-yl]carboxamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 3.44 (3H, OCH₃), 3.64 (2H, —CH₂— of C₂), 3.94 (3H, 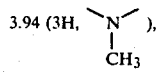), 4.30 (2H, —CH₂S— of C₃), 5.18 (1H, H of C₆), 5.62 (1H, 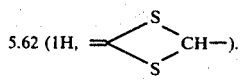).

Reference example 10:

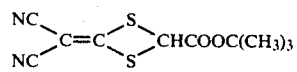

To 15 ml. of methylene chloride was added 0.28 g. of tert-butyl 4-[(carbamoyl)(cyano)methylene]-1,3-dithietane-2-carboxylate obtained in Reference example 7. After adding thereto 0.33 g. of pyridine and 0.43 g. of phosphorus pentachloride, the mixture was stirred for 30 minutes at room temperature. Then, 30 ml. of chloroform was added to the reaction mixture and the mixture was washed with 1 normal sulfuric acid, a 5% aqueous sodium carbonate solution, and then a saturated aqueous sodium chloride solution. The mixture was then dried over anhydrous magnesium sulfate and the solvent was distilled off under reduced pressure. The residue formed was subjected to a silica gel column chromatography to provide 0.23 g. of tert-butyl 4-dicyanomethylene-1,3-dithietan-2-carboxylate using chloroform as the eluant.

Nuclear magnetic resonance spectra (CDCl₃)

δ(p.p.m.): 1.54 (9H, —COOC(CH₃)₃)

5.02 (1H, 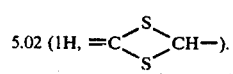).

Reference example 11:

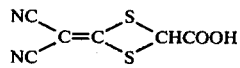

To 0.23 g. of tert-butyl 4-dicyanomethylene-1,3-dithietane-2-carboxylate obtained in Reference example 9 were added 2 ml. of anisole and 6 ml. of trifluoroacetic acid, and the mixture was stirred for 3 hours at room temperature. The solvents were distilled off under reduced pressure and 10 ml. of hexane was mixed with the residue followed by stirring for 10 minutes. The solvent was removed by decantation. Then the same procedure was applied twice to the residue thus formed. The residue was then dried under reduced pressure to provide 0.18 g. of 4-dicyanomethylene-1,3-dithietane-2-carboxylic acid.

EXAMPLE 14

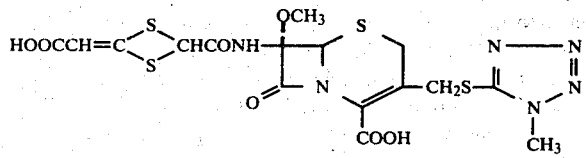

(a) In 20 ml. of methylene chloride was dissolved 0.714 g. of 4-(tert-butoxycarbonylmethylene)-1,3-dithietane-2-carboxylic acid. Then 0.454 g. of pyridine was added to the solution followed by cooling to a temperature below 5° C. Thereafter, 0.630 g. of phosphorus pentachloride was added to the mixture to cause the reaction for one hour at a temperature below 10° C. The reaction mixture obtained was cooled to about −50° C. and a solution prepared by dissolving 1.5 g. of 7β-amino-7α-methoxy-3-(1-methyltetrazol-5-yl)-thiomethyl-Δ³-cephem-4-carboxylic acid benzhydryl ester in 15 ml. of methylene chloride was added dropwise to the reaction mixture. Then, 3 ml. of pyridine was added and the reaction was performed for 1 hour at −30° C. to −35° C. After the reaction was over, 20 ml. of 6 normal hydrochloric acid was added to the reaction mixture at a temperature below 0° C. The methylene chloride layer formed was recovered and the aqueous layer was further extracted with 20 ml. of methylene chloride. The extract was combined with the methylene chloride layer and the mixture was washed twice each time with 20 ml. of a saturated aqueous sodium chloride solution, dried over anhydrous magnesium sulfate, and then the solvent was distilled off to provide 1.89 g. of a brown caramel residue. The residue was subjected to a silica gel column chromatography to provide 0.308 g. of 7β-[(4-tert-butoxycarbonylmethylene)-1,3-dithietan-2-yl]carboxamido-7α-methoxy-3-(1-methyltetrazol-5-yl)thiomethyl-Δ³-cephem-4-carboxylic acid benzhydryl ester using a mixture of ethyl acetate and n-hexane of 2:1 by volume ratio as the eluant.

Nuclear magnetic resonance spectra (D₆-DMSO)

δ(p.p.m.): 1.40 (9H, tert-butyl), 3.44 (3H, OCH₃), 3.88 (3H, 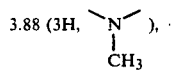), 5.23 (1H, H of C₆), 5.33 (1H, 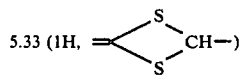)

5.84 (1H, 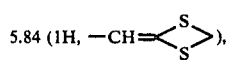), 6.88 (1H, —CH(C₆H₅)₂)

9.66 (1H, —CONH—).

(b) In 1.7 ml. of anisole was dissolved 0.3 g. of the product obtained in aforesaid step (a). After cooling the solution to a temperature below −5° C., 5.1 ml. of trifluoroacetic acid was added dropwise to the solution at a temperature below 0° C. Thereafter, the reaction was performed for 30 minutes at 0°–5° C. and then for 30 minutes at 5°–10° C. After the reaction was over, anisole and trifluoroacetic acid were distilled off under reduced pressure and the residue was powdered with the addition of ether. The powder was washed well with ether, and dried to provide 0.1584 g. of faint-yellow powdery 7β-[4-(carboxymethylene)-1,3-dithietan-2-yl]carboxamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 3.43 (3H, OCH₃), 3.94 (3H, 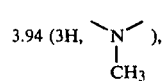), 5.17 (1H, H of C₆), 5.33 (1H, 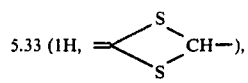), 5.84 (1H, 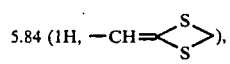), 9.63 (1H, —CONH—)

Reference example 12

A mixture of 80 ml. of dimethoxyethane and 20 ml. of tetrahydrofuran deoxygenated by distillation was cooled below −70° C. in a nitrogen stream and after adding thereto 2 ml. of N-isopropylcyclohexylamine and 6.86 ml. of a 15% n-butyl lithium n-hexane solution, 1.16 g. of tert-butyl acetate was added dropwise to the mixture. Then, the reaction was performed for 30 minutes at a temperature below −70° C. and then 0.664 ml. of carbon disulfide was added to the reaction mixture over a period of about 30 minutes at a temperature below −72° C. The reaction mixture colored light yellow. After further causing the reaction for 20 minutes at a temperature below −70° C., 6.8 ml. of 15% n-butyl lithium n-hexane solution was added dropwise to the reaction mixture over a period of 15 minutes at a temperature below −72° C. Thereafter, the reaction was further performed for 20 minutes at a temperature below −70° C. and then a solution containing crystals of sodium diiodoacetate prepared from 0.48 g. of 50% sodium hydride and 3.12 g. of diiodoacetic acid in 15 ml. of dimethoxyethane was added to the reaction mixture. The temperature of the reaction mixture was allowed to raise to room temperature and the reaction mixture was further reacted overnight. The solvent was distilled off and the black-brown oily material obtained was extracted with the additions of 50 ml. of cold ether and 20 ml. of 1 normal hydrochloric acid.

The aqueous layer was further extracted with the addition of 30 ml. of cold ether and the extracts were combined. The mixture was washed twice each time with 30 ml. of a saturated aqueous sodium chloride solution, dried over anhydrous magnesium sulfate, and then ether was distilled off to provide 3 g. of a brown oily product. The product was subjected to a silica gel column chromatography to provide 0.564 g. of 4-(tert-butoxycarbonylmethylene)-1,3-dithietane-2-carboxylic acid using a mixture of chloroform, methanol, and formic acid of 95:5:2 by volume ratio as the eluant.

Nuclear magnetic resonance spectra (D₆-DMSO)

δ(p.p.m.): 1.45 (9H, tert-butyl), 5.03 (1H, 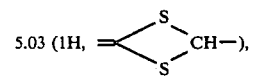), 5.69 (1H, 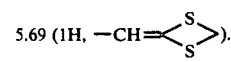).

EXAMPLE 15

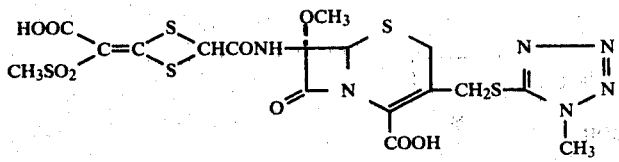

(a) In 8 ml. of methylene chloride was dissolved 0.32 g. of 7β-amino-7α-methoxy-3-(1-methyltetrazol-5-yl)thiomethyl-Δ³-cephem-4-carboxylic acid benzhydryl ester. After cooling the solution to −30° C., 0.48 g. of pyridine was added to the solution. Then, a solution prepared by dissolving 0.37 g. of 4-[(tert-butoxycarbonyl)(methylsulfonyl)methylene]-1,3-dithietane-2-carboxylic acid in 8 ml. of methylene chloride and adding thereto 0.25 g. of phosphorus petachloride and 0.18 g. of pyridine was added dropwise to the solution at a temperature of −40° C. to −30° C. After stirring the mixture for one hour at −30° C. to −20° C., 50 ml. of chloroform was added to the mixture and the resultant mixture was washed with 1% hydrochloric acid, water, and then a saturated aqueous sodium chloride solution, and dried over anhydrous magnesium sulfate. The solvent was distilled off under reduced pressure and the residue was subjected to a silica gel column chromatography to provide 0.25 g. of 7β-{4-[(tert-butoxycarbonyl)(methylsulfonyl)methylene]-1,3-dithietan-2-yl}carboxamido-7α-methoxy-3-(1-methyltetrazol-5-yl)thiomethyl-Δ³-cephem-4-carboxylic acid benzhydryl ester using a mixture of chloroform and isopropanol of 40:1 by volume ratio as the eluant.

Nuclear magnetic resonance spectra (CDCl₃)

δ(p.p.m.): 1.54 (9H, tert-butyl)

3.18 (3H, $CH_3SO_2$ >= ), 3.58 (3H, $OCH_3$), 3.84 (3H, N-CH₃ ), 4.16 (2H, —CH₂— of C₃), 5.07 (1H, H of C₆), 5.31 (1H, =$<^S_S$CH), 6.91 (1H, —CH(C₆H₅)₂), 7.30 (10H, —CH(C₆H₅)₂).

(b) To 2.5 ml. of anisole was added 0.2 g. of the product obtained in step (a). The solution was cooled to −20° C., and then 10 ml. of trifluoroacetic acid was added dropwise to the mixture at −20° C. to −10° C., Then, after stirring the mixture for 20 minutes at the same temperature, the mixture was further stirred for 40 minutes at 10° C. The solvent was distilled off under reduced pressure, the residue formed was mixed with 30 ml. of ether, and the mixture was stirred for 20 minutes. The reaction mixture was filtered under reduced pressure and the precipitates thus obtained were washed well with ether and dried under reduced pressure to provide 0.08 g. of 7β-{4-[(carboxy)(methylsulfonyl)methylene]-1,3-dithietan-2-yl}carboxamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 3.20 (3H, $CH_3SO_2$ >= ), 3.45 (3H, $OCH_3$), 3.62 (2H, —CH₂— of C₂), 3.94 (3H, N-CH₃ ), 4.30 (2H, —CH₂— of C₃), 5.13 (1H)
5.17 (1H) } H of C₆ and =$<^S_S$CH—

Reference example 13:

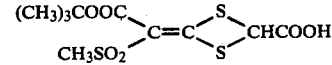

In 65 ml. of tert-butanol was dissolved 2.05 g. of tert-butyl methylsulfonylacetate. After adding thereto 1.32 g. of potassium tert-butylate, the mixture was stirred for 5 minutes. After adding dropwise 0.91 g. of carbon disulfide to the mixture and stirring them for 5 minutes, 1.32 g. of potassium tert-butylate was added to the mixture followed by stirring for one hour. Then, 3.8 g. of diiodoacetic acid and 1.32 g. of potassium tert-butylate were added to the mixture and the resultant mixture was stirred overnight. The solvent was distilled off from the reaction mixture obtained under reduced pressure. The residue formed was mixed with water, adjusted to pH 2 with 10% hydrochloric acid, and extracted with ethyl acetate. The extract was washed with water and then a saturated aqueous sodium chloride solution, dried over anhydrous magnesium sulfate, and then the solvent was distilled off under reduced pressure. The residue was subjected to a silica gel column chromatography to provide 1.7 g. of 4-[(tert-butoxycarbonyl)(methylsulfonyl)methylene]-1,3-dithietane-2-carboxylic acid using a mixture of chloroform and methanol of 50:1 by volume ratio as the eluant.

Nuclear magnetic resonance spectra (CDCl₃)

δ(p.p.m.): 1.52 (9H, (CH₃)₃COOC—)
3.20 (3H, CH₃SO₂—).

EXAMPLE 16

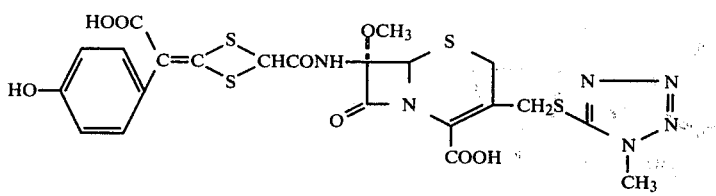

(a) In 1.5 ml. of methylene chloride was dissolved 0.6 g. of 4-(4-tert-butoxy-α-tert-butoxycarbonylbenzylidene)-1,3-dithietane-2-carboxylic acid. After adding thereto 0.2 ml. of pyridine and further 0.285 g. of phosphorus pentachloride under ice-cooling, the mixture was stirred for 7 minutes. The solution was added to a solution prepared by dissolving 0.5 g. of 7β-amino-7α-methoxy-3-(1-methyltetrazol-5-yl)thiomethyl-Δ³-cephem-4-carboxylic acid benzhydryl ester in 15 ml. of methylene chloride, cooling to −30° C. to −40° C., and adding thereto 0.45 ml. of pyridine, and the mixture was stirred for 20 minutes at the same temperature.

The reaction mixture was mixed with 60 ml. of chloroform, washed with about 30 ml. of water, about 30 ml. of 1–2% hydrochloric acid, and then 30 ml. of water, dried over anhydrous magnesium sulfate, and then the solvent was distilled off under reduced pressure. The residue was subjected to a silica gel column chromatography to provide 0.4 g. of 7β-[4-(4-tert-butoxy-α-tert-butoxycarbonylbenzylidene)-1,3-dithietan-2-yl]carboxamido-7α-methoxy-3-(1-methyltetrazol-5-yl)-thiomethyl-Δ³-cephem-4-carboxylic acid benzhydryl ester using a mixture of benzene and ethyl acetate of 11:2 by volume ratio as the eluant.

Nuclear magnetic resonance spectra (CDCl₃)

δ(p.p.m.): 1.35 (9H),
1.47 (9H), } tert-butyl 3.60 (5H, OCH₃ and —CH₂— of C₂), 3.83 (3H, >N<),
       |
       CH₃

4.83 (1H, =<S\S>CH—), 5.08 (1H, H of C₆), 6.92 (1H, —CH(C₆H₅)₂)

6.94 (2H)
7.15 (2H) } HO—⟨phenyl⟩

(b) In a mixture of 10 ml. of trifluoroacetic acid and 2 ml. of anisole was dissolved 0.4 g. of the product obtained in step (a) under ice-cooling. The mixture was stirred for about 30 minutes at 10° C. The solvent was distilled off under reduced pressure and 40 ml. of ether was added to the residue to form precipitates, which were recovered by filtration and washed with ether to provide about 0.2 g. of 7β-[4-(α-carboxy-4-hydroxybenzylidene)-1,3-dithietan-2-yl]carboxamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 3.42 (3H, OCH₃), 3.94 (3H, >N<),
        |
        CH₃

5.15 (2H, H of C₆ and =<S\S>CH—), 6.74 (2H)
7.03 (2H) } HO—⟨phenyl⟩

Reference example 14:

(CH₃)₃COOC\
           C=C<S\S>CHCOOH
(CH₃)₃CO—⟨phenyl⟩

To 8.6 ml. of a 15% potassium tert-butylate tert-butanol solution were added 2.5 g. of tert-butyl 4-tert-butoxyphenylacetate and 25 ml. of anhydrous tetrahydrofuran with stirring at room temperature. After stirring the mixture for 2–3 minutes, 0.6 ml. of carbon disulfide was added dropwise to the mixture followed by stirring for 10 minutes. Then, 8.6 ml. of a 15% potassium tert-butylate tert-butanol solution was added to the mixture followed by stirring for 5 minutes, further 8.6 ml. of a 15% potassium tert-butylate tert-butanol solution was added to the mixture and then 1.22 g. of dichloroacetic acid was added dropwise to the mixture at about 30° C. followed by stirring for 40 minutes at room temperature.

Then, after adding dichloroacetic acid to the reaction mixture until the mixture became weak alkaline, the solvent was distilled off under reduced pressure and the residue was mixed with ice-water followed by washing with ether. Then, 0.5 ml. of 3 normal hydrochloric acid was added to the mixture and the product was extracted with ether. To the extract was further added 0.5 ml. of 3 normal hydrochloric acid. The product was extracted with ether, and the procedure was further repeated. Each extract fraction obtained was detected by a silica gel thin layer chromatography, the fractions containing the product were collected and dried over anhydrous magnesium sulfate. Then, the solvent was distilled off under reduced pressure to provide 1.3 g. of 4-(4-tert-butoxy-α-tert-butoxycarbonylbenzilidene)-1,3-dithietane-2-carboxylic acid.

Nuclear magnetic resonance spectra (D$_6$-DMSO)

(p.p.m.): 1.35 (9H) }
4.85 (9H) } (CH$_3$)$_3$C—,

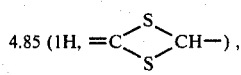

4.85 (1H, 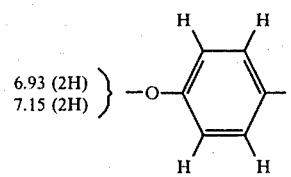), 6.93 (2H) }
7.15 (2H) } 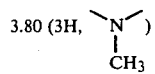

EXAMPLE 17

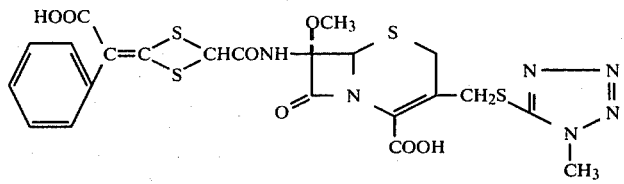

(a) In 15 ml. of methylene chloride was dissolved 0.5 g. of 4-(α-tert-butoxycarbonylbenzylidene)-1,3-dithietane-2-carboxylic acid. After adding thereto 0.2 ml. of pyridine and further 0.285 g. of phosphorus petachloride under ice-cooling, the mixture was stirred for about 20 minutes. Then, by treating the reaction mixture as in Example 16-(a) using, however, a mixture of benzene and ethyl acetate of 9:2 by volume ratio as the eluant for silica gel column chromatography, about 0.4 g. of 7β-[4-(α-tert-butoxycarbonylbenzylidene)-1,3-dithietane-2-yl]carboxamido-7α-methoxy-3-(1-methyltetrazol-5-yl)thiomethyl-Δ$^3$-cephem-4-carboxylic acid benzhydryl ester was obtained.

Nuclear magnetic resonance spectra (CDCl$_3$)

δ(p.p.m.): 1.46 (9H, tert-butyl), 3.58 (5H, OCH$_3$ and —CH$_2$— of C$_2$), 3.80 (3H, ⟩N⟨ )
        |
        CH$_3$ 4.85 (1H, 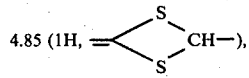), 5.08 (1H, H of C$_6$), 6.93 (1H, —CH(C$_6$H$_5$)$_2$), about 7.34 (15H, C$_6$H$_5$— and (C$_6$H$_5$)$_2$CH—).

(b) By treating 0.4 g. of the product obtained in above step (a) as in Example 16-(b), about 0.2 g. of 7β-[4-(α-carboxybenzylidene)-1,3-dithietane-2-yl]carboxamido-7α-methoxy-3-(1-methyltetrazol-5-yl)thiomethyl-Δ$^3$-cephem-4-carboxylic acid was obtained.

Nuclear magnetic resonance spectra (D$_6$-DMSO)

δ(p.p.m.): 3.41 (3H, OCH$_3$), 3.92 (3H, ⟩N⟨ ),
         |
         CH$_3$ 5.16 (1H) }
5.19 (1H) } H of C$_6$ and 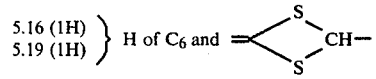

7.28 (5H, C$_6$H$_5$—).

Reference example 15:

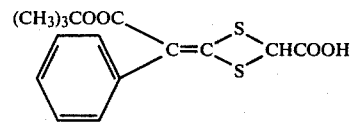

To 15.6 g. of a 15% potassium tert-butylate tert-butanol solution were added 4 g. of tert-butyl phenylacetate and then 1.6 g. of carbon disulfide with stirring at room temperature. After stirring the mixture for 15 minutes, 20 ml. of anhydrous tetrahydrofuran and then 31.2 g. of a 15% potassium tert-butylate tert-butanol solution were added to the mixture and then 2.7 g. of dichloroacetic acid was added dropwise to the mixture at 30°–40° C. followed by stirring for 30 minutes at the same temperature to finish the reaction.

Then, after adding dichloroacetic acid to the reaction mixture until the mixture became weakly alkaline, the solvent was distilled off under reduced pressure and the residue was mixed with ice-water followed by washing with ether. Then, 0.5 ml. of 3 normal hydrochloric acid was added to the mixture and the product was extracted with ether. To the extract was further added 0.5 ml. of 3 normal hydrochloric acid. The product was extracted with ether, and the procedure was further repeated. Each extract fraction obtained was detected by a silica gel thin layer chromatography, the fractions containing the objective material were collected and dried over anhydrous magnesium sulfate. Then, the solvent was distilled off under reduced pressure to provide about 1 g. of 4-(α-tert-butoxycarbonylbenzylidene)-1,3-dithietane-2-carboxylic acid.

Nuclear magnetic resonance spectra (D$_6$-DMSO)

δ(p.p.m.): 1.40 (9H, (CH$_3$)$_3$COOC—), 5.17 (1H, 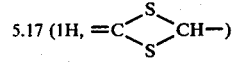)

about 7.30 (5H, 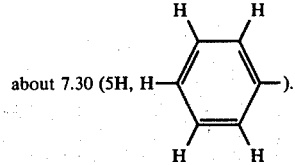).

EXAMPLE 18

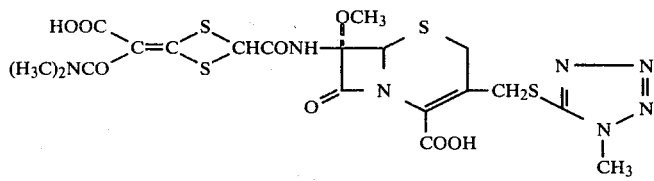

(a) In 15 ml. of methylene chloride was dissolved 500 mg. of 4-(tert-butoxycarbonyl-N,N-dimethylcarbamoylmethylene)-1,3-dithietane-2-carboxylic acid. After adding thereto 0.19 ml. of pyridine and further 163 mg. of phosphorus pentachloride under ice-cooling, the mixture was stirred for about 5 minutes. The solution was added to a solution prepared by dissolving 500 mg. of 7β-amino-7α-methoxy-3-(1-methyltetrazol-5-yl)thiomethyl-Δ³-cephem-4-carboxylic acid in 15 ml. of methylene chloride and then adding 0.3 ml. of pyridine to the solution while cooling the solution to −30° C., and the mixture was stirred for about 30 minutes at the same temperature.

To the reaction mixture was added about 60 ml. of chloroform. The mixture was washed with about 30 ml. of water, about 30 ml. of 1-2% hydrochloric acid, and then three times each time with about 30 ml. of water, and dried over anhydrous magnesium sulfate. The solvent was distilled off under reduced pressure and the residue formed was subjected to a silica gel column chromatography to provide 200 mg. of 7β-[(4-tert-butoxycarbonyl-N,N-dimethylcarbamoylmethylene)-1,3-dithietane-2-yl-carboxamido]-7α-methoxy-3-(1-methyltetrazol-5-yl)thiomethyl-Δ³-cephem-4-carboxylic acid benzhydryl ester using a mixture of benzene and ethyl acetate of 3:2 by volume ratio as the eluant.

Nuclear magnetic resonance spectra (CDCl₃)

δ(p.p.m.): 1.48 (9H, tert-C₄H₉—), 2.96 (6Hm (CH₃)₂NCO—)

3.60 (5H, CH₃O and —CH₂— of C₂), 3.84 (3H, CH₃—N $\begin{matrix}\diagup=N\\ \\ \diagdown\\ N=N\end{matrix}$ )

4.93 (1H, =C$\begin{matrix}S\\ \\ S\end{matrix}$CHCO—)

5.06 (1H, H of C₆), 6.90 (1H, —CH(C₆H₅)₂).

(b) In a mixture of 10 ml. of trifluoroacetic acid and 2 ml. of anisole was dissolved the product obtained in above step (a) under ice-cooling. And the mixture was stirred for about 30 minutes at 15° C. The solvent was distilled off under reduced pressure, 30 ml. of ether was added to the residue, and the precipitates formed were recovered by filtration and washed with ether to provide 100 mg. of 7β-[(4-carboxy-N,N-dimethylcarbamoylmethylene)-1,3-dithietane-2-yl-carboxamido]-7α-methoxy-3-(1-methyltetrazole-5-yl)-thiomethyl -Δ³-cephem-4carboxylic acid.

Nuclear magnetic resonance spectra (D₆-DMSO)

δ(p.p.m.): 2.87 (6H, (CH₃)₂NCO—), 3.43 (3H, CH₃O—),

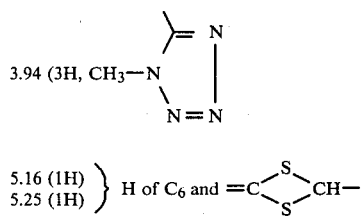

5.16 (1H) }
5.25 (1H) } H of C₆ and =C$\begin{matrix}S\\ \\ S\end{matrix}$CH—

Reference example 16:

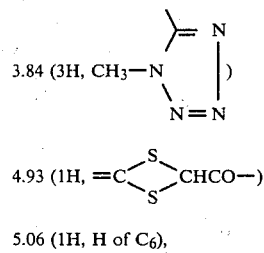

By treating tert-butyl dimethylcarbamoylacetate as in Reference example 15, 4-[(tert-butoxycarbonyl)-(dimethyl carbamoyl)methylene]-1,3-dithietane-2-carboxylic acid was obtained.

Nuclear magnetic resonance spectra (CDCl₃)

δ(p.p.m.): 1.50 (9H, (CH₃)₃COOC—), 3.02 (6H, $\begin{matrix}CH_3\\ \\ CH_3\end{matrix}$ N—), 4.97 (1H, =C$\begin{matrix}S\\ \\ S\end{matrix}$CH—).

EXAMPLE 19

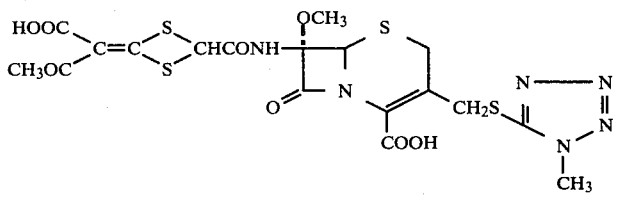

(a) In 15 ml. of methylene chloride was dissolved 0.87 g. of 4-[(acetyl)(tert-butoxycarbonyl)methylene)-1,3-dithietane-2-carboxylic acid. After adding thereto 0.474 g of pyridine and further 0.624 g. of phosphorus pentachloride under ice-cooling, the mixture was stirred for 30 minutes. The solution was added to a solution prepared by dissolving 0.6 g. of 7β-amino-7α-methoxy-3-(1-methyltetrazol-5-yl)-thiomethyl-Δ³-cephem-4-carboxylic acid benzhydryl ester in 20 ml. of methylene chloride, cooling the solution to −30° C., and adding thereto 1 ml. of pyridine, and the mixture was stirred for one hour at the same temperature. To the reaction mixture were added 10 ml. of water, 1 ml. of 1 normal hydrochloric acid, and 30 ml. of chloroform. The chloroform layer formed was recovered, washed thoroughly with 1% hydrochloric acid to eliminate pyridine completely, then with water, dried over anhydrous sodium sulfate, and the solvent was distilled off under reduced pressure. The residue formed was subjected to a silica gel column chromatography to provide 0.55 g. of 7β-{4-[(acetyl)(tert-butoxycarbonyl)methylene]-1,3-dithietan-2-yl}carboxamido-7α-methoxy-3-(1-methyltetrazol-5-yl)thiomethyl-Δ³-cephem-4-carboxylic acid benzhydryl ester using a mixture of benzene and ethyl acetate of 10:2 by volume ratio as the eluant.

Nuclear magnetic resonance spectra (CDCl₃)

δ(p.p.m.): 1.53 (9H, tert-butyl), 2.45 (3H, CH₃OC—), 3.56 (5H, OCH₃ and —CH₂— of C₂), 3.82 (3H, 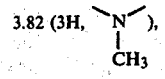), 4.37 (2H, —CH₂S— of C₃), 4.94 (1H, 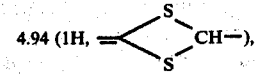), 5.09 (1H, H of C₆), 6.94 (1H, =CH(C₆H₅)₂), 7.20–7.50 (10H, —CH(C₆H₅)₂).

(b) In a mixture of 12 ml. of trifluoroacetic acid and 3 ml. of anisole was dissolved 0.55 g. of the product obtained in aforesaid step (a) at −5° C. The mixture was stirred for 20 minutes at 15° C. The solvent was distilled off under reduced pressure, 20 ml. of ether was added to the residue, and the precipitates formed were recovered by filtration and washed with ether to provide 0.33 g. of 7β-{4-[(acetyl)(carboxy)methylene]-1,3-dithietan-2-yl}carboxamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 2.38 (3H, CH₃OC—), 3.43 (3H, OCH₃), 3.94 (3H, ), 4.32 (2H, —CH₂S— of C₃), 5.16 (1H)  
5.30 (1H) } H of C₆ and 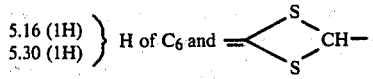

Reference example 17:

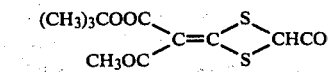

To 150 ml. of tert-butanol was added 4.8 g. of sodium hydride (50% in oil). Then 15.8 g. of tert-butyl acetoacetate was added gradually to the mixture. Then, after adding thereto 7.6 g. of carbon disulfide under ice-cooling, the mixture was stirred for 18 hours at room temperature. Thereafter, 4.8 g. of sodium hydride (50% in oil) was added gradually under ice-cooling and after stirring the mixture for 2 hours at room temperature, 16.7 g of potassium dichloroacetate was added to the mixture followed by stirring for further 2 hours. The reaction mixture obtained was concentrated under reduced pressure. The residue was mixed with 300 ml. of ethyl acetate and 200 ml. of ice-water, and the mixture was adjusted to pH 3–4 with 1 normal hydrochloric acid. The organic layer formed was washed with an aqueous sodium chloride solution, and extracted with a saturated aqueous sodium hydrogencarbonate solution. The sodium hydrogencarbonate extract was washed with 50 ml. of ethyl acetate, adjusted to pH 3–4 with 1 normal hydrochloric acid, and extracted with 200 ml. of ethyl acetate. The ethyl acetate extract was washed with an aqueous sodium chloride solution, dried over anhydrous sodium sulfate, and then concentrated. The residue was washed with 50 ml. of a mixture of petroleum ether and ether of 10:1 by volume ratio and dissolved in 5 ml. of ether. Then, 50 ml. of petroleum ether was added gradually to the solution and the crystals thus precipitated were recovered by filtration to provide 10 g. of 4-[(acetyl)(tert-butoxycarbonyl)methylene]-1,3-dithietane-2-carboxylic acid.

Nuclear magnetic resonance spectra (CDCl₃)

δ(p.p.m.): 1.53 (9H, (CH₃)₃COOC—), 2.49 (3H, CH₃OC—), 4.94 (1H, 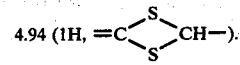).

EXAMPLE 20

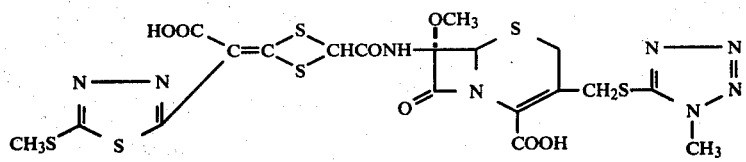

(a) In 20 ml. of methylene chloride was dissolved 1.1 g. of 4-[(tert-butoxycarbonyl)(5-methylthio-1,3,4-thiadiazol-2-yl)methylene]-1,3-dithietane-2-carboxylic acid. After adding thereto 0.462 g. of pyridine and further 0.606 g. of phosphorus pentachloride under ice-cooling, the mixture was stirred for 30 minutes. The solution was added to a solution prepared by dissolving 0.9 g. of 7β-amino-7α-methoxy-3-(1-methyltetrazol-5-yl)thiomethyl-Δ³-cephem-4-carboxylic acid benzhydryl ester in 30 ml. of methylene chloride, cooling the solution to −30° C., and adding 0.75 ml. of pyridine to the solution, and the mixture was stirred for one hour at room temperature. The reaction mixture was mixed with 10 ml. of water and 40 ml. of chloroform. Then, the chloroform layer formed was washed thoroughly with 1% hydrochloric acid to eliminate pyridine completely, then with water, dried over anhydrous sodium sulfate, and then the solvent was distilled off under reduced pressure. The residue was subjected to a silica gel column chromatography to provide 0.2 g. of 7β-{4-[(tert-butoxycarbonyl)(5-methylthio-1,3,4-thiadiazol-2-yl)methylene]-1,3-dithietan-2-yl}carboxamido-7α-methoxy-3-(1-methyltetrazol-5-yl)thiomethyl-Δ³-cephem-4-carboxylic acid benzhydryl ester using a mixture of benzene and ethyl acetate of 10:2 by volume ratio as the eluant.

Nuclear magnetic resonance spectra (CDCl₃)

δ(p.p.m.): 1.58 (9H, tert-butyl), 2.72 (3H, CH₃S—), 3.58 (3H, OCH₃), 3.80 (3H, 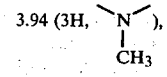), 4.36 (2H, —CH₂S— of C₃), 5.03 (1H)
5.09 (1H)  } H of C₆ and 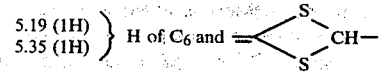

6.90 (1H, —CH(C₆H₅)₂), 7.10-7.50 (10H, —CH(C₆H₅)₂).

(b) In a mixture of 8 ml. of trifluoroacetic acid and 2 ml. of anisole was dissolved 0.2 g. of the product obtained in above step (a) at −5° C. followed by stirring for one hour at 17°-18° C. The solvent was distilled off under reduced pressure, 20 ml. of ether was added to the residue, and the precipitates formed were recovered by filtration and washed with ether to provide 0.05 g. of 7β-{4-[(carboxy)(5-methylthio-1,3,4-thiadiazol-2-yl)methylene]-1,3-dithietan-2-yl}-carboxamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 2.75 (3H, CH₃S—), 3.45 (3H, OCH₃), 3.94 (3H, 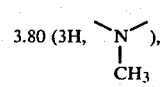), 4.30 (2H, —CH₂S— of C₃), 5.19 (1H)
5.35 (1H)  } H of C₆ and 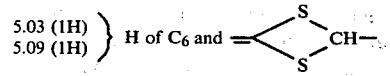

Reference example 18:

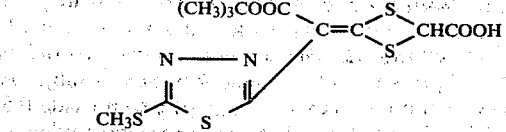

100 ml. of tert-butanol was dissolved 1.58 g. of metallic potassium. After adding thereto 10 g. of tertbutyl 5-methylthio-1,3,4-thiadiazole-2-acetate, the mixture was stirred for 20 minutes. Thereafter, 3.25 g. of carbon disulfide was added dropwise to the mixture over a period of 10 minutes. After stirring the mixture for one hour, 4.55 g. of potassium tert-butyrate was added gradually to the mixture followed by stirring for 20 minutes and then 6.83 g. of potassium dichloroacetate was added to the mixture followed by stirring for 18 hours. The reaction mixture was concentrated under reduced pressure, and the residue was mixed with 300 ml. of ethyl acetate and 200 ml. of ice-water. The mixture was adjusted to pH 3-4 with 1 normal hydrochloric acid, and the organic layer formed was washed with an aqueous sodium chloride solution, and then extracted with 1000 ml. of a saturated aqueous sodium hydrogencarbonate solution. The sodium hydrogencarbonate extract was washed with 100 ml. of ethyl acetate, adjusted to pH 3-4 with 5 normal hydrochloric acid, and then extracted with 200 ml. of ethyl acetate. The ethyl acetate extract was washed with an aqueous sodium chloride solution, dried over anhydrous sodium sulfate, and concentrated. The residue was subjected to a silica gel column chromatography to provide 1 g. of 4-[(tert-butoxycarbonyl)(5-methylthio-1,3,4-thiadiazol-2yl)methylene]-1,3-dithietane-2-carboxylic acid using chloroform and then a mixture of chloroform and methanol of 50:1 by volume ratio as the eluant.

Nuclear magnetic resonance spectra (CDCl₃)

δ(p.p.m.): 1.59 (9H, (CH₃)₃COOC—), 2.79 (3H, CH₃S—), 4.99 (1H, ).

Example 21

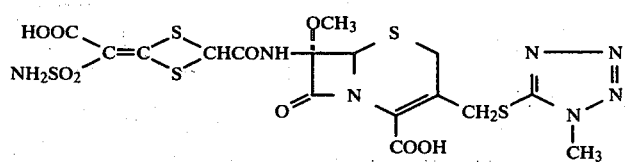

(a) In 12 ml. of anhydrous tetrahydrofuran were dissolved 0.2 g. of 4-[(benzhydryloxycarbonyl)(sulfamoyl)methylene]-1,3-dithietane-2-carboxylic acid, 0.25 g. of 7β-amino-7α-methoxy-3-(1-methyltetrazol-5-yl)thiomethyl-Δ³-cephem-4-carboxylic acid benzhydryl ester, and 0.1 g. of N,N'-dicyclohexylcarbodiimide.

Then the solution was stirred overnight at room temperature. Insoluble materials were filtered off and the solvent was distilled off from the filtrate under reduced pressure. The residue was subjected to a silica gel column chromatography to provide 0.095 g. of 7β-{4-[(benzhydryloxycarbonyl)(sulfamoyl)methylene]-1,3-dithietan-2-yl}carboxamido-7α-methoxy-3-(1-methyltetrazol-5-yl)thiomethyl-Δ³-cephem-4-carboxylic acid benzhydryl ester using a mixture of chloroform and isopropanol of 9:1 by volume ratio as the eluant.

(b) In 10 ml. of methylene chloride was dissolved 0.095 g. of the product obtained in step (a). After adding thereto 0.5 ml. of anisole, the mixture was cooled to −20° C. Thereafter, 2 ml. of trifluoroacetic acid was added dropwise to the mixture at −20° C. to −15° C. and after stirring the mixture for 30 minutes at the same temperature, the resultant mixture was further stirred for one hour at 0°–3° C. The solvent was distilled off from the reaction mixture under reduced pressure and 15 ml. of ether was added to the residue followed by stirring for 30 minutes. Then, the reaction mixture was filtered under reduced pressure and the precipitates formed were washed well and dried under reduced pressure to provide 0.034 g. of 7β-{4-[(carboxy)(sulfamoyl)methylene]-1,3-dithietan-2-yl}carboxamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 3.42 (3H, OCH₃), 3.94 (3H, 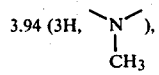), 4.30 (2H, —CH₂— of C₃), 5.12 (1H) }
5.17 (1H) }  H of C₆ and 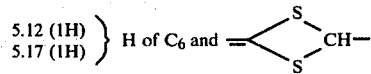

9.66 (1H, —NHCO—).

Reference example 19:

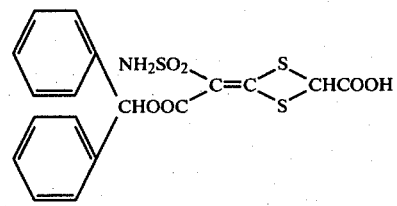

1.12 g. of benzhydryl sulfamoylacetate were added 30 ml. of anhydrous tetrahydrofuran and 20 ml. of tert-butanol.

After cooling the mixture to −20° C., 0.177 g. of sodium hydride (50% in oil) was added to the mixture followed by stirring for 15 minutes. To the mixture was added 0.3 g. of carbon disulfide. The mixture was stirred for 30 minutes at −10° C. to −5° C. Then, to the mixture were added 0.354 g. of sodium hydride (50% in oil) and 1.05 g. of diiodoacetic acid. After stirring the mixture for 20 minutes at −10° C. to 0° C., the mixture was stirred overnight at room temperature. The solvent was distilled off from the reaction mixture under reduced pressure and after adjusting the residue to pH 2 by adding thereto ice-water and 5% hydrochloric acid, the reaction mixture was extracted with ethyl acetate. The extract was washed twice each time with a saturated aqueous sodium chloride solution, dried over anhydrous magnesium sulfate, and then the solvent was distilled under reduced pressure. The residue was subjected to a silica gel column chromatography to provide 0.2 g. of 4-[(benzhydryloxycarbonyl)(sulfamoyl)methylene]-1,3-dithietane-2-carboxylic acid using a mixture of chloroform and methanol of 10:1 by volume ratio as the eluant.

Nuclear magnetic resonance spectra (CDCl₃)

δ(p.p.m.): 4.66 (1H, =C<S,S>CH—), 6.96 (1H, (C₆H₅)₂CH—)

7.33 (10H, (C₆H₅)₂CH—).

EXAMPLE 22

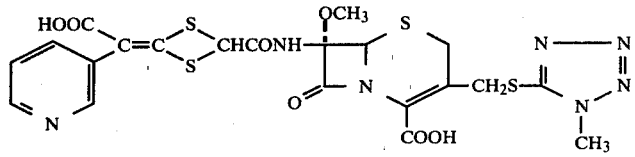

(a) In 40 ml. of methylene chloride was dissolved 800 mg. of 4-[(tert-butoxycarbonyl)(3-pyridyl)methylene]-1,3-dithietane-2-carboxylic acid. After adding thereto 0.3 ml. of pyridine and further 440 mg. of phosphorus pentachloride under ice-cooling, the mixture was stirred for about 15 minutes. The solution was added to a solution prepared by dissolving 0.8 g. of 7β-amino-7α-methoxy-3-(1-methyltetrazol-5-yl)thiomethyl-Δ³-cephem-4-carboxylic acid in 25 ml. of methylene chloride and adding thereto 0.7 ml. of pyridine at −30° C., and the resultant mixture was stirred for 20 minutes at the same temperature. Then, 200 ml. of chloroform was added to the reaction mixture and the mixture was washed twice each time with 150 ml. of an aqueous 1.3% acetic acid solution and then twice each time with 100 ml. of water, and then dried over anhydrous magnesium sulfate. The solvent was distilled off under reduced pressure and the residue formed was subjected to a silica gel column chromatography to provide about 400 mg. of 7β-{4-[(tert-butoxycarbonyl)(3-pyridyl)methylene]-1,3-dithietan-2-yl}carboxamido-7α-methoxy-3-(1-methyltetrazol-5-yl)thiomethyl-Δ³-cephem-4-carboxylic acid using a mixture of benzene and ethyl acetate of 2:1 by volume ratio as the eluant.

Nuclear magnetic resonance spectra (CD Cl$_3$)

δ(p.p.m.): 1.47 (9H, t-C$_4$H$_9$—), 3.59 (5H, CH$_3$O— and —CH$_2$— of C$_2$), 3.83 (3H, >N—CH$_3$), 4.91 (1H, 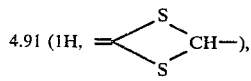), 5.08 (1H, H of C$_6$), 6.93 (1H, —CH(C$_6$H$_5$)$_2$), 8.50 (1H 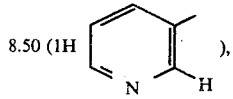), 8.53 (1H, 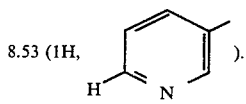).

(b) In a mixture of 15 ml. of trifluoroacetic acid and 3 ml. of anisole was dissolved 400 mg. of the compound obtained in above step (a) under ice cooling followed by stirring for 40 minutes at 10°–15° C. The solvent was distilled off under reduced pressure and about 50 ml. of ether was added to the residue to form precipitates, which were recovered by filtration, and washed with ether. The precipitates were subjected to a silica gel column chromatography to provide about 100 mg. of 7β-{[4-(carboxy)(3-pyridyl)methylene]-1,3-dithietan-2-yl}carboxamido-7α-methoxy-3-(1-methyltetrazol-5-yl)thiomethyl-Δ$^3$-cephem-4-carboxylic acid using a mixture of chloroform, methanol, and formic acid of 50:7:1 by volume ratio as the eluant.

Nuclear magnetic resonance spectra (D$_6$-DMSO)

δ(p.p.m.): about 3.41 (3H, CH$_3$O—).

3.93 (3H, CH$_3$N<), 5.15 (1H)
5.24 (1H) } H of C$_6$ and 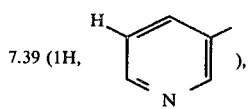, 7.39 (1H, 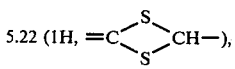), 7.67 (1H, 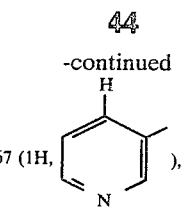), 8.44 (2H, 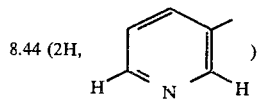)

Reference example 20:

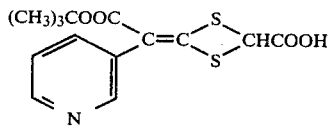

By treating tert-butyl 3-pyridylacetate as in Reference example 15, 4-[(tert-butoxycarbonyl)(3-pyridyl)methylene]-1,3-dithietane-2-carboxylic acid was obtained.

Nuclear magnetic resonance spectra (D$_6$-DMSO)

δ(p.p.m.): 1.42 (9H, (CH$_3$)$_3$COOC—), 5.22 (1H, 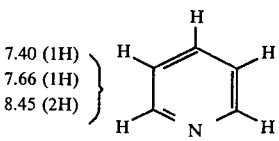), 7.40 (1H)
7.66 (1H)
8.45 (2H) } 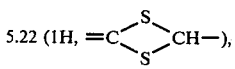

EXAMPLE 23

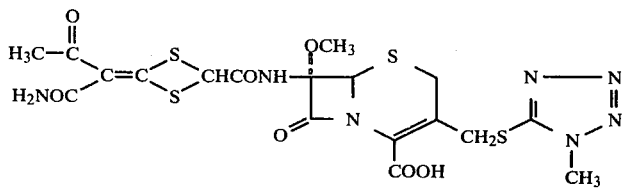

(a) In 55 ml. of anhydrous tetrahydrofuran were dissolved 0.22 g. of 4-[(acetyl)(carbamoyl)methylene]-1,3-dithietane-2-carboxylic acid, 0.496 g. of 7β-amino-7α-methoxy-3-(1-methyltetrazol-5-yl)thiomethyl-Δ$^3$-cephem-4-carboxylic acid benzhydryl ester, and 0.194 g. of N,N′-dicyclohexylcarbodiimide. The solution was stirred for 2 hours at room temperature. Insoluble materials were filtered off and the filtrate was concentrated under reduced pressure. The residue formed was subjected to a silica gel column chromatography to provide 0.35 g. of 7β-{4[(acetyl)(carbamoyl)methylene]-1,3-dithietan-2-yl}carboxamido-7α-methoxy-3-(1-methyletetrazol-5-yl)thiomethyl-Δ$^3$-cephem-4-carboxylic acid benzhydryl ester using first a mixture of chloroform and ethyl acetate of 1:1 by volume ratio and then a mixture of chloroform and ethyl acetate of 1:3 by volume ratio as the eluant.

(b) In a mixture of 8 ml. of trifluoroacetic acid and 2 ml. of anisole was dissolved 0.35 g. of the product obtained in the above step (a) at −20° C. followed by stirring for 30 minutes at 0° C. The reaction mixture obtained was concentrated and the residue was mixed with ether followed by stirring for 30 minutes. Then, the precipitates formed were recovered by filtration and washed with ether to provide 0.09 g. of 7β-{[4-(acetyl)(carbamoyl)methylene]-1,3-dithietan-2-yl}carbxamido-7α-methoxy-3-(1-methyltetrazol-5-yl)thiomethyl-Δ³-cephem-4-carboxylic acid.

Nuclear magnetic resonance spectra (D₆-DMSO)

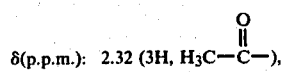

3.42 (3H, CH₃O— of C₇),

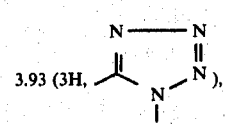

4.30 (2H, —CH₂S— of C₃),

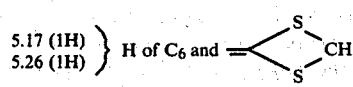

Reference example 21:

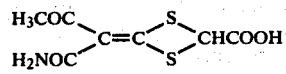

(a) In 50 ml. of tert-butanol was dissolved B 5.76 g. of potassium tert-butylate and 50 ml. of anhydrous tetrahydrofuran was added to the solution. Then, after dissolving therein 2.6 g. of acetoacetamide, a solution prepared by dissolving 1.96 g. of carbon disulfide in 5 ml. of anhydrous tetrahydrofuran was added dropwise to the solution under ice-cooling. To the reaction mixture obtained was added 100 ml. of anhydrous tetrahydrofuran followed by stirring for 1.5 hours at room temperature. Then a suspension prepared by reacting 8 g. of diiodoacetic acid and 1.23 g. of sodium hydride (50% in oil) in 100 ml. of anhydrous tetrahydrofuran under ice-cooling was added to the mixture followed by stirring for 2.5 hours at room temperature.

The reaction mixture obtained was concentrated and the residue was mixed with 50 ml. of 1 normal hydrochloric acid and extracted with 100 ml. of ethyl acetate. The extract was washed with 50 ml. of an aqueous sodium chloride solution and the organic layer formed was extracted with 100 ml. of a saturated aqueous sodium hydrogencarbonate solution. The extract was adjusted to pH 2-3 with concentrated hydrochloric acid and then extracted with 100 ml. of ethyl acetate. The extract was washed with 50 ml. of an aqueous sodium chloride solution, dried over anhydrous magnesium sulfate, and concentrated.

The residue formed was dissolved in 30 ml. of methylene chloride and after adding thereto 5 g. of diphenyldiazomethane under ice-cooling, the mixture was stirred for 2 hours at room temperature. The reaction mixture was concentrated and the residue formed was subjected to a silica gel column chromatography to provide 0.6 g. of 4-[(acetyl)(carbamoyl)-methylene]-1,3-dithietane-2-carboxylic acid benzhydryl ester using first chloroform and then a mixture of chloroform and methanol of 10:2 by volume ratio as the eluant.

Nuclear magnetic resonance spectra (CDCl₃)

δ(p.p.m.): 2.32 (3H, H₃COC—),

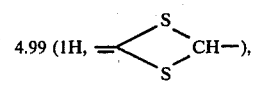

6.97 (1H, —COOCH(C₆H₅)₂), 7.2-7.4 (10H, —COOCH(C₆H₅)₂).

(b) In a mixture of 8 ml. of trifluoroacetic acid and 2 ml. of anisole was dissolved 0.6 g. of the product obtained in the step (a) at −20° C. and the temperature of the reaction mixture was raised to 10° C. over a period of 20 minutes. Then, the reaction mixture was concentrated and 10 ml. of a mixture of ether and petroleum ether of 1:1 by volume ratio was added to the residue to form precipitates, which were recovered by filtration to provide 0.2 g. of 4-[(acetyl)(carbamoyl)methylene]-1,3-dithietane-2-carboxylic acid.

Nuclear magnetic resonance spectra (D₆-DMSO)

δ(p.p.m.): 2.31 (3H, H₃COC—),

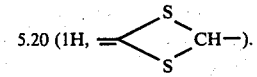

EXAMPLE 24

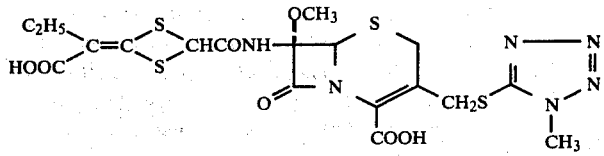

(a) In 15 ml. of tetrahydrofuran was dissolved 610 mg. of 4-(1-tert-butoxycarbonylpropylidene)-1,3-dithietane-2-carboxylic acid after adding thereto 1.05 g. of 7β-amino-7α-methoxy-3-(1-methyltetrazol-5-yl)thiomethyl-Δ³-cephem-4-carboxylic acid benzhydryl ester and 0.5 g. of N,N'-dicyclohexylcarbodiimide, the mixture was stirred for 2 hours at room temperature to cause reaction. After the reaction was over, the N,N'-dicyclohexyl urea product was filtered off and the solvent was distilled off from the filtrate under reduced pressure to form a caramel-like residue. The residue thus formed was dissolved in 50 ml. of ethyl acetate and the solution was washed with 30 ml. of 1 normal hydrochloric acid and then water and dried over anhydrous magnesium sulfate. The solvent was distilled off under reduced pressure to provide 450 mg. of a brown caramel-like residue. The residue was applied to a silica gel column chromatography using 30 g. of silica gel and the product was eluted using first benzene, a mixture of benzene and ethyl acetate of 95:5 by volume ratio, and then a mixture of benzene and ethyl acetate of 90:10 by volume ratio as the eluant, and the fractions containing the product were collected to provide about 10 mg. of 7β-[4-(1-tert-butoxycarboxypropylidene)-1,3-dithietan-2-yl]-carboxamido-7α-methoxy-3-(1-methyltetrazol-5-yl)thiomethyl-Δ³-cephem-4-carboxylic acid benzhydryl ester.

Nuclear magnetic resonance spectra (CDCl₃)

δ(p.p.m.): 1.62 (3H, CH₃, t), 2.08 (9H, (CH₃)₃C—), 2.66 (2H, —CH₂—, q), 4.22 (3H, —OCH₃, s), 4.44 (3H, >N—CH₃, s),

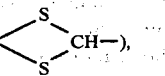

5.40 and 5.47 (H of C₆ and 7.54 (1H, —CH(C₆H₅)₂), 7.8–8.2 (10H, —CH(C₆H₅)₂), 8.30 (1H, —NH—CO—), (b) In 1.1 ml. of anisole was dissolved 200 mg. of the caramel-like product obtained in the above step and the solution was cooled to about 5° C. in an ice-water bath. To the solution was added dropwise 3.3 ml. of trifluoroacetic acid at a temperature below 10° C. and thereafter the mixture was stirred for one hour at 5°–10° C. to cause reaction. Then, anisole and excessive trifluoroacetic acid were distilled off under reduced pressure at a temperature below room temperature and the residue was mixed with 10 ml. of water and extracted with a mixture of n-butanol and ethyl acetate of 1:1 by volume ratio. The organic layer was collected, washed with a saturated aqueous sodium chloride solution, dried over anhydrous magnesium sulfate, and then the solvent was distilled off under reduced pressure. The residue was triturated with 10 ml. of ether to provide 54 mg. of 7β-[4-(1-carboxypropylidene)-1,3-dithietan-2-yl]carboxamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 0.96 (3H, —CH₃, t), 2.00 (2H, —CH₂—, q), 3.41 (3H, —O—CH₃, s), 3.92 (3H, >N—CH₃, s),

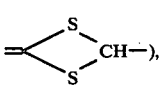

5.10 and 5.16 (H of C₆ and 9.60 (1H, —NHCO—).

Reference example 22:

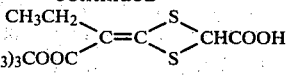
-continued

A mixture of 120 ml. of dimethoxyethane and 30 ml. of tetrahydrofuran was cooled to −74° C. in a dry ice-acetone bath and then 4.0 ml. of N-isopropylcyclohexylamine and then 13.72 ml. of a 15% n-butyl lithium n-hexane solution were added to the mixture, whereby the temperature was raised from −73° C. to −62° C. After adding 3.17 g. of tert-butyl butylate and causing reaction for 30 minutes at −74° C. to −75° C., 0.664 ml. of carbon disulfide was added dropwise to the mixture over a period of 10 minutes followed by reaction for 20 minutes at the temperature. Then, 6.86 ml. of a 15% n-butyl lithium n-hexane solution was added dropwise to the reaction mixture at a temperature below −72° C. over a period of 10 minutes and then they were caused to react for 30 minutes. Then, 0.332 ml. of carbon disulfide was added to the reaction mixture over a period of 10 minutes and the reaction was performed for 20 minutes. Furthermore, 3.43 ml. of a 15% n-butyl lithium n-hexane solution was added dropwise to the reaction mixture at a temperature below −72° C. over a period of 13 minutes and then the reaction was further performed for 20 minutes at −74° C. to −73° C. Moreover, 0.166 ml. of carbon disulfide was added to the reaction mixture at about −74° C. over a period of 6 minutes and the reaction was performed for about 25 minutes. Thereafter, sodium diiodoacetate prepared by reacting 0.84 g. of 50% sodium hydride and 5.46 g. of diiodoacetic acid in 25 ml. of dimethoxyethane was added to the reaction mixture followed by reaction for 30 minutes at 0°–5° C. and then the reaction was further continued overnight at room temperature. The solvent was distilled off under reduced pressure from the reaction mixture and the residue was extracted with the addition of 50 ml. of cold ether and 40 ml. of 1 normal hydrochloric acid. The ether layer obtained was extracted twice each time with 20 ml. of a saturated aqueous sodium hydrogencarbonate solution. The aqueous extracts were combined and adjusted to pH 1 with 1 normal hydrochloric acid, extracted twice with 30 ml. and 20 ml. of ether, successively. The extracts were combined and washed with water, dried over anhydrous magnesium sulfate, and then ether was distilled off to provide 1.08 g. of an oily product. The oily product was applied to a silica gel column chromatography and the fractions containing the product were collected using a mixture of chloroform and methanol of 10:1 by volume ratio to provide 630 mg. of the brown oily 4-(1-carboxypropylidene)-1,3-dithietane-2-carboxylic acid.

Nuclear magnetic resonance spectra (CDCl₃)

δ(p.p.m.): 1.24 (3H, —CH₃, t), 1.47 (9H, (CH₃)₃C—, s), 2.01 (2H, —CH₂—, q),

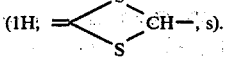

4.87 (1H,

EXAMPLE 25

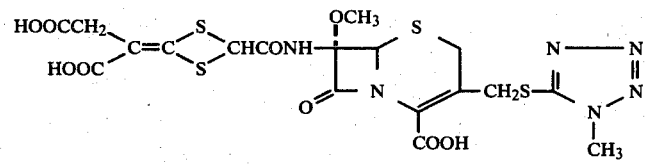

(a) In 10 ml. of tetrahydrofuran was dissolved 350 mg. of 4-[1,2-bis(tert-butoxycarbonyl)ethylidene]-1,3-dithietane-2-carboxylic acid. After adding thereto 0.5 g. of 7β-amino-7α-methoxy-3-(1-methyltetrazol-5-yl)thiomethyl-Δ³-cephem-4-carboxylic acid benzhydryl ester and 219 mg. of N,N'-dicyclohexylcarbodiimide, they were made to react for 2 hours at room temperature. After filtering off the N,N'-dicyclohexylurea thus deposited, the solvent was distilled off from the filtrate, the residue was applied to a silica gel column chromatography and the fractions containing the product were collected using first benzene and then a mixture of benzene and ethyl acetate of 9:1 by volume ratio as the eluant to provide 120 mg. of 7β-{4-[1,2-bis(tert-butoxycarbonyl)-ethylidene]-1,3-dithietan-2-yl}carboxamido-7α-methoxy-3-(1-methyltetrazol-5-yl)thiomethyl-Δ³-cephem-4-carboxylic acid benzhydryl ester.

Nuclear magnetic resonance spectra (CDCl₃)

δ(p.p.m.): 1.42–1.48 (18H, (CH₃)₃C—), 2.58 (2H, —CH₂—), 3.59 (3H, —OCH₃), 3.80 (3H, ⟩N—CH₃), 4.36 (2H, —CH₂— of C₂, q), 4.87 and 5.09 (H of C₆ and =⟨S\S⟩CH—), 6.92 (1H, —CH(C₆H₅)₂), 7.2–7.6 (10H, —CH(C₆H₅)₂).

(b) In 1 ml. of anisole was dissolved 115 mg. of the product obtained in the above step (a). After cooling the solution to a temperature below 10° C. in an ice-water bath, 3 ml. of trifluoroacetic acid was added dropwise to the solution at a temperature below 10° C. After stirring the mixture for one hour at 5°–10° C., excess trifluoroacetic acid and anisole were distilled off from the reaction mixture under reduced pressure at room temperature and the residue formed was triturated with 5 ml. of ether to provide 73.7 mg. of 7β-[4-(1,2-dicarboxyethylidene)-1,3-dithietan-2-yl]carboxamido-7α-methoxy-3-(1-methyltetrazol-5-yl)thiomethyl-Δ³-cephem-4-carboxylic acid.

Nuclear magnetic resonance spectra (D₆-DMSO)

δ(p.p.m.): 3.94 (3H, ⟩N—CH₃), 4.30 (2H, —CH₂— of C₂), 5.16 and 5.20 (H of C₆, =⟨S\S⟩CH—), -continued HOOCCH₂\C= overlapped the DMSO peak.

—OCH₃ overlapped the peak of water.

Reference example 23:

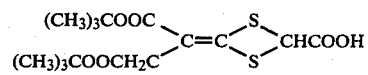

To a mixture of 80 ml. of diethylene glycol dimethyl ether and 20 ml. of tetrahydrofuran was added 1.54 ml. of diisopropylamine. The mixture was cooled to −74° C. with dry ice-acetone bath. Then, 6.86 ml. of a 15% n-butyl lithium n-hexane solution was added to the mixture followed by reaction for 10 minutes at −72° C. to −74° C. Furthermore, 2.3 g. of tert-butyl succinate was added to the reaction mixture and the reaction was further carried out for 30 minutes at −74° C. Then, 0.332 ml. of carbon disulfide was added dropwise to the reaction mixture over a period of about 15 minutes and then the reaction was continued for 15 minutes at −74° C. Also, 3.43 ml. of a 15% n-butyl lithium n-hexane solution was added dropwise to the reaction mixture at a temperature below −71° C. over a period of 20 minutes and the reaction was carried out for 20 minutes at the same temperature. Thereafter, 0.166 ml. of carbon disulfide was added dropwise to the reaction mixture over a period of 13 minutes at a temperature below −72° C. and the reaction was carried out for 17 minutes at the temperature. Moreover, 1.715 ml. of a 15% n-butyl lithium n-hexane solution was added dropwise to the reaction mixture over a period of 10 minutes at a temperature below −71° C. Finally, 0.083 ml. of carbon disulfide was added dropwise to the reaction mixture over a period of 10 minutes and then the reaction was further carried out for 20 minutes at −72° C. to −74° C.

Separately, a suspension of sodium diiodoacetate prepared beforehand from 432 mg. of 50% sodium hydride and 2.8 g. of diiodoacetic acid in 20 ml. of diethylene glycol dimethyl ether dropwise to the reaction mixture obtained in the aforesaid reaction, whereby the temperature in the system raised from −74° C. to −64° C. Then, the temperature was allowed to raise and after carrying out the reaction for one hour at 0°–5° C., the mixture was stirred overnight at room temperature to cause a further reaction. Thereafter, the solvent was distilled off at room temperature under reduced pressure to provide a brown residue. The residue was mixed with 50 ml. of ether and 20 ml. of a cold 10% sulfuric acid and extracted with ether. The ether layer formed was extracted twice each time with 50 ml. of a saturated sodium hydrogencarbonate solution. The aqueous layer obtained was mixed with 50 ml. of 10% sulfuric acid and extracted with 50 ml. and 30 ml. of ether, successively. The ether extracts were combined and washed

52 of a saturated aqueous solution, dried over anhydrous magnesium sulfate, and ether was distilled off to provide 1.83 g. of an oily product. The oily product was applied to a silica gel column chromatography using 70 g. of silica gel, eluted using first chloroform and then a mixture of chloroform and methanol of 50:1 by volume ratio, and the fractions containing the product were collected to provide 700 mg. of 4-[1,2-bis(tert-butoxycarbonyl)]-1,3-dithietane-2-carboxylic acid.

Nuclear magnetic resonance spectra (CDCl₃)

δ(p.p.m.): 1.22 (18H, 2 × (CH₃)₃C—), 2.58 (2H, —CH₂—), 4.91 (1H, 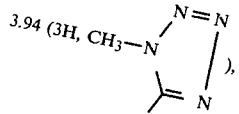).

Mass spectra:

m/e: 362 M+

EXAMPLE 26

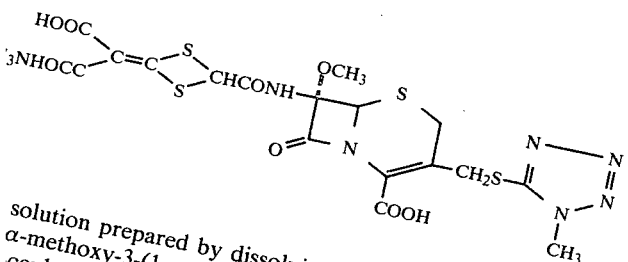

solution prepared by dissolving 500 mg. of α-methoxy-3-(1-methyltetrazol-5-yl)thio-cephem-4-carboxylic acid benzhydryl ester in tetrahydrofuran was added 500 mg. of 4-(carbonyl)-(N-methylcarbamoyl)methylene-dithietane-2-carboxylic acid and about 400 mg. dicyclohexylcarbodiimide, and the mixture was stirred for 3.5 hours at room temperature. The solvent was distilled off from the reaction mixture under reduced pressure and the residue formed was subjected to silica gel column chromatography to provide 1 g. of 7β-{4-[(carboxy)(N-methylcarbamoyl)methylene]-1,3-dithietan-2-yl}carboxamido-7α-methoxy-3-(1-methyltetrazol-5-yl)thiomethyl-Δ³-cephem-4-carboxylic acid benzhydryl ester using a mixture chloroform and ethyl acetate of 4:1 by volume ratio.

Nuclear magnetic resonance spectra (CDCl₃)

... t-C₄H₉—),

... CH₃NHCO—),

... CH₃O— and —CH₂— of C₂),

-continued 6.93 (1H, —CH(C₆H₅)₂).

(b) In a mixture of 10 ml. of trifluoroacetic acid and 2 ml. of anisole was dissolved 300 mg. of the product obtained in the above step (a) under ice-cooling. The solution was stirred for about one hour at 15° C. The solvent was distilled off from the reaction mixture under reduced pressure and the residue was mixed with ether followed by stirring. The precipitates thus formed were recovered by filtration and washed with ether to provide 170 mg. of 7β-{4-[(carboxy)(N-methylcarbamoyl)methylene]-1,3-dithietan-2-yl}carboxamido-7α-methoxy-3-(1-methyltetrazol-5-yl)thiomethyl-Δ³-cephem-4-carboxylic acid.

Nuclear magnetic resonance spectra (D₆-DMSO)

(p.p.m.): 2.68 (3H, CH₃NHCO—), 3.42 (3H, CH₃O—), 3.94 (3H, CH₃—N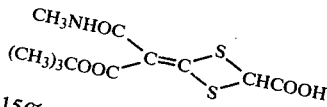), about 5.12 (2H, H of C₆ and =C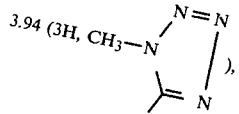).

Reference example 24

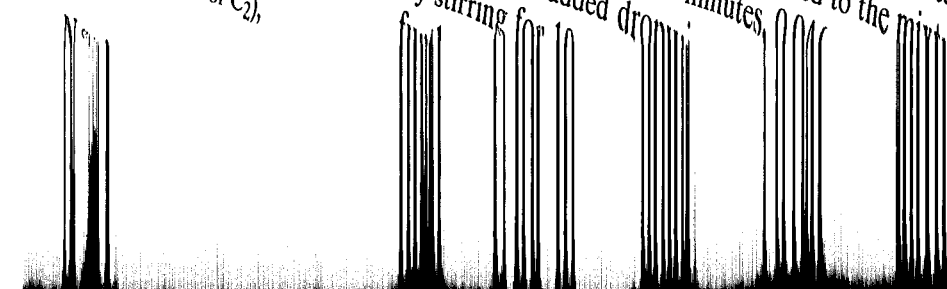

To 3 ml. of 15% potassium tert-butylate tert-butanol solution were added 540 mg. of tert-butyl N-methyl-malonamate and 12 ml. of anhydrous tetrahydrofuran with stirring at room temperature. After stirring the mixture for 5 minutes, 0.0935 ml. of carbon disulfide was added dropwise to the mixture followed by stirring for 10 minutes. Then, 1.5 ml. of 15% potassium tert-butylate tert-butanol solution was added to the mixture followed by stirring for 10 minutes, and carbon disulfide was added dropwise twice each time with 50 ml. of water. Then, ether layer was extracted with 50 ml. of 2% sodium hydrogencarbonate, and the aqueous layer was neutralized to about pH 7.5 with 1 normal hydrochloric acid and extracted with 100 ml. of ether. To the aqueous layer was further added 0.5 ml. of 1 normal hydrochloric acid, and extracted with 100 ml. of ether. This procedure was repeated. Each ether extract was subjected to a silica gel thin layer chromatography using a mixture of acetonitrile, ethylacetate and water of 3:1:1 by volume ratio as the eluant and then fractions containing the product were collected and the solvent was distilled off under reduced pressure to provide 600 mg. of oily 4-[(tert-butoxycarbonyl)(methylcarbamoyl)-methylene]-1,3-dithietane-2-carboxylic acid.

Nuclear magnetic resonance spectra (CDCl$_3$)

(p.p.m.): 1.52 (9H, (CH$_3$)$_3$C—), 2.84 (3H, CH$_3$NH—), 4.83 (1H,  CH—).

EXAMPLE 27

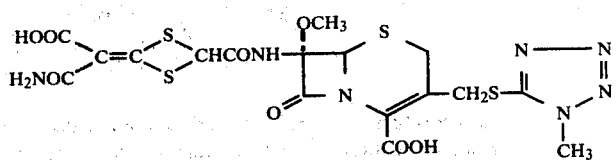

In 8 ml. of an aqueous 5% sodium hydrogencarbonate solution was dissolved 200 mg. of 7β-(4-carboxy-3-hydroxyisothiazol-5-yl)thioacetamido-7α-methoxycephalosporanic acid. The solution was stirred for 2 hours at room temperature. After the reaction was over, the reaction mixture obtained was adjusted to pH 1 with 2 normal hydrochloric acid and then extracted twice each time with a mixture of n-butanol and ethyl acetate of 1:1 by volume ratio. The organic layer was washed with a saturated aqueous sodium chloride solution, dried over anhydrous magnesium sulfate, and the solvent was distilled off to provide 180 mg (90% yield) of white-powdery 7β-{4-[(carbamoyl)-(carboxy)methylene]-1,3-dithietan-2-yl}carboxamido-7α-methoxy-Δ$^3$-cephalosporanic acid.

Nuclear magnetic resonance spectra (D$_6$-DMSO)

(p.p.m.): 5.20 (1H, 

5.12 (1H,  CH—, s), 4.82 (2H, S-CH (H, H), q), 3.48 (2H, =C-CH$_2$O—, q), 3.44 (3H, OCH$_3$, s), 2.04 (3H, —OCOCH$_3$, s).

(b) In 6 ml. of water were added 300 mg. of 7β-[4-(carbamoyl)(carboxy)methylene-1,3-dithietan-2-yl]carboxamido-7α-methoxy cephalosporanic acid, 67.2 mg. of 5-mercapto-1-methyltetrazole and 146 mg. of sodium hydrogencarbonate followed by stirring for 16 hours at 60°-62° C. The reaction mixture was adjusted to pH 1 with 2 normal hydrochloric acid under ice-cooling, and the precipitates formed were recovered by filtration, and dried over phosphorus pentoxide under reduced pressure to provide 75 mg. of light yellow powdery 7β-[4-(carbamoyl)(carboxy)methylene-1,3-dithietan-2-yl]carboxamido-7α-methoxy-3-(1-methyltetrazol-5-yl)thiomethyl-Δ$^3$-cephem-4-carboxylic acid.

EXAMPLE 28

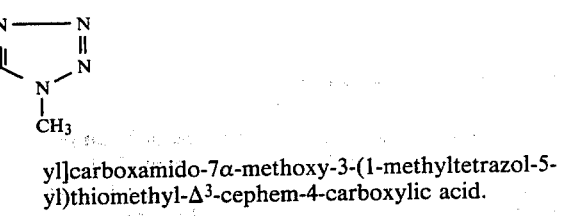

(a) In 60 ml. of methanol was dissolved 6.1 g. of 7β-bromoacetamido-7α-methoxy-cephalosporanic acid.

Then 15 ml. of an ice cooled aqueous solution of 4.3 g. of trisodium salt (trihydrate) of 4-carboxy-3-hydroxy-5-mercaptoisothiazole was added dropwise to the solution at 0°-5° C. After stirring the mixture for 30 minutes at the same temperature, methanol was distilled off under reduced pressure. The residue was mixed with 40 ml. of water, adjusted to pH 3 with 2 normal hydrochloric acid, and washed with ethyl acetate. The aqueous layer was further adjusted to pH 1 with 2 normal hydrochloric acid and then extracted twice each time with a mixture of n-butanol and ethyl acetate of 1:1 by volume ratio. The organic layer was washed with a saturated aqueous sodium chloride solution, dried over anhydrous magnesium sulfate, and the solvent was distilled off to provide a powdery crude product. The product was dissolved in a small amount of methanol and the solution was allowed to cool with ice to form crystals. The crystals were recovered by filtration to provide 4.8 g. (64.2% yield) of the purified white crystals of 7β-(4-carboxy-3-hydroxyisothiazol-5-yl)thioacetamido-7α-methoxycephalosporanic acid.

Nuclear magnetic resonance spectra (D$_6$-DMSO)

δ(p.p.m.): 5.20 (1H, [H–C–S, –N–], s), 4.84 (2H, [S–C(H)(H)], q), 4.02 (2H, [C(=O)SCH$_2$CO–], s), 3.52 (2H, [C(=O)CH$_2$O–], q), 3.44 (3H, [OCH$_3$], s), 2.04 (3H, –OCOCH$_3$, s).

(b) By following the same procedure as in Example 27(b) using 7β-(4-carboxy-3-hydroxyisothiazol-5-yl)thioacetoamido-7α-methoxy-cephalosporanic acid and 5-mercapto-1-methyltetrazole, 7β-(4-carboxy-3-hydroxyisothiazol-5-yl)thioacetamido-7α-methoxy-3-(1-methyltetrazol-5-yl)thiomethyl-Δ$^3$-cephem-4-carboxylic acid was obtained.

EXAMPLE 29

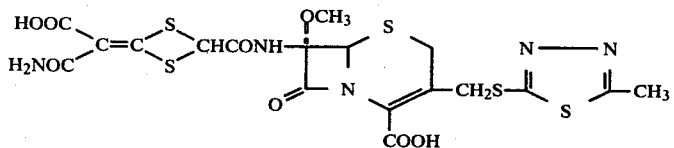

A mixture of 300 mg. of 7β-(4-carboxy-3-hydroxyisothiazol-5-yl)thioacetamido-7α-methoxycephalosporanic acid, 76.5 mg. of 2-mercapto-5-methyl-1,3,4-thiadiazole, 146 mg. of sodium hydrogencarbonate, and 6 ml. of water was stirred for 12 hours at 58°–60° C. The reaction mixture was cooled, adjusted to pH 1 with 2 normal hydrochloric acid under ice-cooling, and the precipitates formed were recovered by filtration, and dried over phosphorus pentoxide under reduced pressure to provide 95 mg. (27.8% yield) of light yellow powdery 7β-{4-[(carbamoyl)(carboxy)methylene]-1,3-dithietan-2-yl}-carboxamido-7α-methoxy-3-(5-methyl-1,3,4-thiadiazol-2-yl)thiomethyl-Δ$^3$-cephem-4-carboxylic acid.

Nuclear magnetic resonance spectra (D$_6$-DMSO)

δ(p.p.m.): 5.16 (1H, [H–C–S, –N–], s), 5.12 (1H, [S–CH–S, S], s), 4.34 (2H, [S–C(H)(H)], q), 3.58 (2H, [C(=O)CH$_2$O–], q), 3.40 (3H, OCH$_3$, s), 2.60 (3H, [–N, C(=S)CH$_3$], s).

EXAMPLE 30

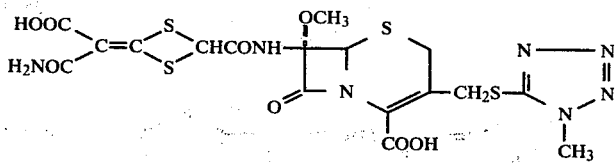

In a mixture of 40 ml. of methanol and 300 ml. of a 5% aqueous sodium hydrogencarbonate solution was dissolved 6.0 g. of 7β-(4-carboxy-3-hydroxyisothiazol-5-yl)thioacetamido-7α-methoxy-3-(1-methyltetrazol-5-yl)thiomethyl-Δ$^3$-cephem-4-carboxylic acid. The solution was stirred for 5 hours at room temperature. The solution was washed with 300 ml. of ethyl acetate, acidified with diluted hydrochloric acid, and extracted twice each time with 200 ml. of a mixture of n-butanol and ethyl acetate of 1:1 by volume ratio and once with 100 ml. of the same mixture. The organic layers were combined with each time other, washed twice each with 50 ml. of a saturated aqueous sodium chloride solution, dried over anhydrous magnesium sulfate, and then the solvent was distilled off under reduced pressure. To the residue was added 50 ml. of ether and precipitates formed were recovered by filtration, washed with ether and dried to provide crude product. The crude product was purified by a silica gel column chromatography using a mixture of chloroform, methanol, and formic acid of 100:20:1.5 by volume ratio as the eluent.

The fractions containing the product were collected and the solvent was distilled off under reduced pressure to provide 3.5 g. of 7β-{4-[(carbamoyl)(carboxy)methylene]-1,3-dithietan-2-yl}carboxamido-7α-methoxy-3-(1-methyltetrazol-5-yl)thiomethyl-Δ$^3$-cephem-4-carboxylic acid.

Nuclear magnetic resonance spectra (D$_6$-DMSO)

δ(p.p.m.): 3.40 (3H, CH₃O— of C₇), 3.61 (2H, —CH₂— of C₂), 3.92 (3H, 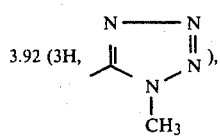), 4.30 (2H, 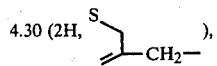), 5.11 (1H)  
5.14 (1H) } H of C₆ and 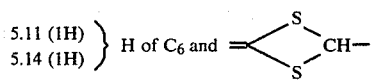

6.00 (1H, —COOH), 7.50 (2H, —CONH₂), 9.60 (1H, —CONH 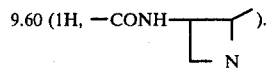 ).

EXAMPLE 31

A mixture of 300 mg. of 7β-(4-carboxy-3-hydroisothiazol-5-yl)thioacetamido-7α-methoxycephalosporanic acid, 67.2 mg. of 5-mercapto-1-methyltetrazole, 146 mg. of sodium hydrogen-carbonate, and 6 ml. of water was stirred for 12 hours at 58°–60° C. The reaction mixture was cooled, adjusted to pH 1 with 2 normal hydrochloric acid in under ice-cooling, and the precipitates formed were recovered by filtration, and dried over phosphorus pentoxide under reduced pressure to provide 7β-{4[(carbamoyl)(carboxy)methylene]-1,3-dithietan-2-yl}carboxamido-7α-methoxy-3-(1-methyltetrazol-5-yl)thiomethyl-Δ³-cephem-4-carboxylic acid.

EXAMPLE 32

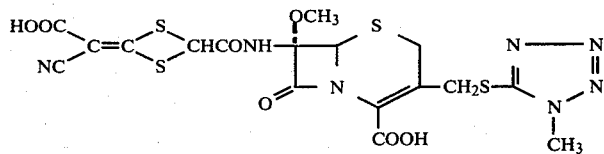

(a) In a mixture of 50 ml. of chloroform and 10 ml. of acetone was suspended 1.0 g. of 7β-{4-[(carbamoyl)-(carboxy)-methylene]-1,3-dithietan-2-yl}carboxamido-7α-methoxy-3-(1-methyltetrazol-5-yl)thiomethyl-Δ³-cephem-4-carboxylic acid.

A solution the prepared by dissolving about 700 mg. of diphenyldiazomethane in 5 ml. of chloroform and the solution was added dropwise to the suspension. The mixture was stirred for 30 minutes at room temperature and then the solvent was distilled off from the reaction mixture. The residue was subjected to a silica gel column chromatography using a mixture of chloroform and ethyl acetate of 2:1 by volume ratio as the eluant to isolate and purify the product. Thus, the fractions containing the product were collected and the solvent was distilled off under reduced pressure to provide 0.8 g. of 7β-{4-[(benzhydryloxycarbonyl)(carbamoyl)methylene]-1,3-dithietan-2-yl}carboxamido-7α-methoxy-3-(1-methyltetrazol-5-yl)thiomethyl-Δ³-cephem-4-carboxylic acid benzhydryl ester.

Nuclear magnetic resonance spectra (CDCl₃)

δ(p.p.m.): 3.52 (5H, H of C₂ and CH₃O— of C₇), 3.76 (3H, 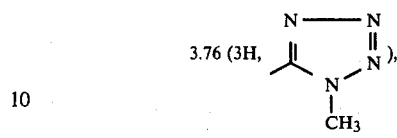), 4.35 (2H, —CH₂—S— of C₃), 4.86 (1H, 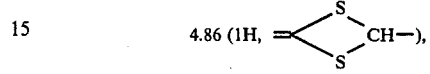), 5.00 and 5.03 (1H, H of C₆), 6.90 (1H)  
7.00 (1H) } —CH(C₆H₅)₂), 7.30 (10H, —CH(C₆H₅)₂).

(b) In 10 ml. of chloroform was dissolved 1.0 g. of 7β-{4-[(benzhydryloxycarbonyl)(carbamoyl)methylene)-1,3-dithietan-2-yl}carboxamido-7α-methoxy-3-(1-methyltetrazol-5-yl)thiomethyl-Δ³-cephem-4-carboxylic acid benzhydryl ester. While stirring the solution under ice-cooling, 0.3 ml. of pyridine and 0.45 g. of phosphorus pentachloride were added to the solution followed by stirring further for one hour at room temperature. The reaction mixture was then ice-cooled and 3 ml. of water was added to the mixture. The organic layer formed was separated from an aqueous layer, washed with 2 ml. of water, dried over anhydrous magnesium sulfate, and then the solvent was distilled off under reduced pressure to provide 0.5 g. of 7β-{4-[(benzhydryloxycarbonyl)(cyano)methylene)-1,3-dithietan-2-yl}-carboxamido-7α-methoxy-3-(1-methyltetrazol-5-yl)thiomethyl-Δ³-cephem-4-carboxylic acid benzhydryl ester.

Nuclear magnetic resonance spectra (CDCl₃)

δ(p.p.m.): 345 (5H, H of C₂ and CH₃O— of C₇), 3.80 (3H, 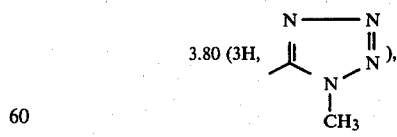), 4.32 (2H, —CH₂—S— of C₃), 5.02 (2H, H of C₆ and 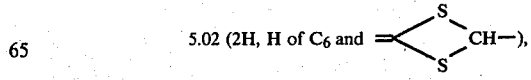

6.85 (2H, —CH(C₆H₅)₂),

-continued
7.30 (10H, —CH(C$_6$H$_5$)$_2$).

(c) In 2 ml. of methylene chloride was dissolved 0.5 g. of 7β-{4-[(benzhydryloxycarbonyl)(cyano)methylene]-1,3-dithietan-2-yl}carboxamido-7α-methoxy-3-(1-methyltetrazol-5-yl)thiomethyl-Δ$^3$-cephem-4-carboxylic acid benzhydryl ester. After adding thereto 5 ml. of a mixture of trifluoroacetic acid and anisole in a 4:1 by volume ratio at −10° C., the mixture was stirred for 30 minutes at the same temperature. Then, the solvent was distilled off under reduced pressure at a low temperature from the reaction mixture. The residue was triturated with ether and was recovered by filtration and dried to provide 0.2 g. of powdery 7β-{4-[(carboxy)(cyano)methylene]-1,3-dithietan-2-yl}carboxamido-7α-methoxy-3-(1-methyltetrazol-5-yl)thiomethyl-Δ$^3$-cephem-4-carboxylic acid.

Nuclear magnetic resonance spectra (D$_6$-DMSO)

δ(p.p.m.): 3.44 (3H, CH$_3$O— of C$_7$), 3.62 (2H, H of C$_2$), 4.30 (2H, —CH$_2$—S—), 5.16 (1H, H of C$_6$), 5.52 (1H, 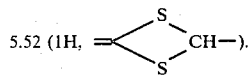 CH—).

By the same procedure as in Example 1, the following compounds were obtained.

EXAMPLE 33

7β-(4-cyano-3-hydroxyisothiazol-5-yl)thioacetamido-7α-methoxy-3-(1-methyltetrazol-5-yl)thiomethyl-Δ$^3$-cephem-4-carboxylic acid.

Nuclear magnetic resonance spectra (D$_6$-DMSO)
δ(p.p.m.): 3.39 (3H), 3.59 (2H), 3.92 (3H), 4.11 (2H), 4.28 (2H), 5.10 (1H).

EXAMPLE 34

7β-(3-hydroxy-4-phenylisothiazol-5-yl)thioacetamido-7α-methoxy-3-(1-methyltetrazol-5-yl)thiomethyl-Δ$^3$-cephem-4-carboxylic acid.

Nuclear magnetic resonance spectra (D$_6$-DMSO)
δ(p.p.m.): 3.40 (3H), 3.56 (2H), 3.87 (2H), 3.92 (3H), 4.27 (2H), 5.05 (1H).

EXAMPLE 35

7β-(3-amino-4-cyanoisothiazol-5-yl)thioacetamido-7α-methoxy-3-(1-methyltetrazol-5-yl)thiomethyl-Δ$^3$-cephem-4-carboxylic acid.

Nuclear magnetic resonance spectra (D$_6$-DMSO)
δ(p.p.m.): 3.40 (3H), 3.60 (2H), 3.95 (3H), 4.08 (2H), 4.31 (2H), 5.11 (1H).

EXAMPLE 36

7β-(4-dimethylcarbamoyl-3-hydroxyisothiazol-5-yl)-thioacetamido-7α-methoxy-3-(1-methyltetrazol-5-yl)thiomethyl-Δ$^3$-cephem-4-carboxylic acid.

Nuclear magnetic resonance spectra (D$_6$-DMSO)
δ(p.p.m.): 2.88 (6H), 3.38 (3H), 3.56 (2H), 3.90 (5H), 4.26 (2H), 5.04 (1H).

EXAMPLE 37

7β-(3-hydroxyisothiazol-4-yl)thioacetamido-7α-methoxy-3-(1-methyltetrazol-5-yl)thiomethyl-Δ$^3$-cephem-4-carboxylic acid.

Nuclear magnetic resonance spectra (D$_6$-DMSO)
δ(p.p.m.): 3.39 (3H), 3.48 (2H), 3.66 (2H), 3.94 (3H), 4.26 (2H), 5.11 (1H), 7.59 (1H).

EXAMPLE 38

7β-(4-cyano-2-methyl-3-oxo-2,3-dihydroisothiazol-5-yl)thioacetamido-7α-methoxy-3-(1-methyltetrazol-5-yl)-thiomethyl-Δ$^3$-cephem-4-carboxylic acid.

Nuclear magnetic resonance spectra (D$_6$-DMSO)
δ(p.p.m.): 3.40 (3H), 3.64 (2H), 3.92 (8H), 4.30 (2H), 5.16 (1H).

EXAMPLE 39

7β-[4-cyano-2-(2-hydroxyethyl)-3-oxo-2,3-dihydroisothiazol-5-yl]thioacetamido-7α-methoxy-3-(1-methyltetrazol-5-yl)thiomethyl-Δ$^3$-cephem-4-carboxylic acid.

Nuclear magnetic resonance spectra (D$_6$-DMSO)
(p.p.m.): 3.40 (3H), 3.5–3.6 (3H), 3.76 (2H), 3.93 (3H), 4.16 (2H), 4.32 (2H), 5.14 (1H).

EXAMPLE 40

7β-(4-carbamoyl-3-hydroxyisothiazol-5-yl)thioacetamido-7α-methoxy-3-(1-methyltetrazol-5-yl)thiomethyl-Δ$^3$-cephem-4-carboxylic acid.

Nuclear magnetic resonance spectra (D$_6$-DMSO)
δ(p.p.m.): 3.39 (3H), 3.49 (2H), 3.64 (2H), 3.93 (3H), 4.28 (2H), 5.07 (1H)

EXAMPLE 41

7β-(3-hydroxy-4-hydroxymethylisothiazol-5-yl)thioacetamido-7α-methoxy-3-(1-methyltetrazol-5-yl)thiomethyl-Δ$^3$-cephem-4-carboxylic acid.

Nuclear magnetic resonance spectra (D$_6$-DMSO)
δ(p.p.m.): 3.40 (3H), 3.58 (2H), 3.83 (2H), 3.92 (3H), 4.12 (2H), 4.30 (2H), 5.10 (1H).

EXAMPLE 42

In 7 ml. of methylene chloride was dissolved 300 mg. of 7β-amino-7α-methoxy-3-(1-methyltetrazol-5-yl)thiomethyl-Δ$^3$-cephem-4-carboxylic acid benzhydryl ester, chilled to −30° C. and 460 mg. of pyridine was added. Separately, an acid chloride solution was prepared from the suspension of 240 mg. of potassium (4-cyano-3-methoxyisothiazol-5-yl)thioacetate in 10 ml. of methylene chloride, 170 mg. of oxalyl chloride and a drop of dimethylformamide. The acid chloride solution was added dropwise to the above solution at −30° C. to −20° C. and stirred for one hour at the same temperature. To the reaction mixture was added 30 ml. of chloroform and washed twice each time with 2% hydrochloric acid and twice each time with saturated sodium hydrogencarbonate. The organic layer was then separated and dried over anhydrous magnesium sulfate. The organic layer was condensed under reduced pressure and the residue obtained was subjected to silica gel column chromatography with the eluant of a mixture of chloroform and isopropanol (10:1 by volume ratio). There was thus obtained 190 mg. of 7β-(4-cyano-3-methoxyisothiazol-5-yl)thioacetamido-7α-methoxy-3-(1-methyltetrazol-5-yl)thiomethyl-Δ$^3$-cephem-4-carboxylic acid benzhydryl ester.

In 2 ml. of methylene chloride was dissolved the above product and a mixture of 1.6 ml. of trifluoroacetic acid and anisole (3:1 by volume ratio) was added dropwise at −15° C. to −5° C. and stirred for 40 minutes at the same temperature. The solvent was distilled off under reduced pressure, the residue was triturated with 10 ml. of ether, filtered and dried under reduced pressure to provide 120 mg. of a powder of 7β-(4-cyano-3-methoxyisothiazol-5-yl)thioacetamido-7α-methoxy-3-(1-methyltetrazol-5-yl)thiomethyl-Δ³-cephem-4-carboxylic acid.

Nuclear magnetic resonance spectra ($D_6$-DMSO) (p.p.m.): 3.40 (3H), 3.58 (2H), 3.92 (3H), 3.99 (3H), 4.15 (2H), 4.18 (2H), 5.12 (1H).

What is claimed is:

1. A process for the preparation of a 7α-methoxy-7β-(4-substituted methylene-1,3-dithientane-2-yl) carboxamido-3-heterocyclic thiomethyl-Δ³-cephem-4-carboxylic acid represented by the formula

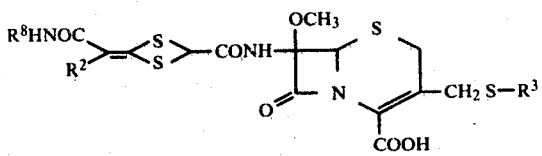

wherein $R^2$ represents a hydrogen atom, a lower alkyl group, a lower alkoxy group, $R^4S(O)_n$ group wherein $R^4$ represents a lower alkyl gorup and n represents 0, 1 or 2, a lower alkanoyl group, a phenyl group, a naphthyl group, a benzoyl group, a napthoyl group, a lower alkenyl group a sulfamoyl group, or a pyridyl group, or a thiadiazolyl group, and $R^3$ represents a lower alkyl-substituted tetrazolyl group or a lower alkyl-substituted thiadiazolyl group, and $R^8$ represents a hydrogen atom or an alkyl group which may have substituents selected from N-monoalkyl carbamoyl, N-dialkyl carbamoyl, and alkoxy carbonyl amino, which comprises treating the 7α-methoxy-3-heterocyclic thiomethyl-cephalosporin derivatives represented by the formula

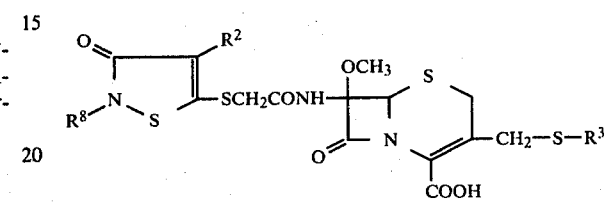

wherein $R^2$, $R^3$ and $R^8$ have the same significance as above, with a base.

2. The method of claim 1, wherein said base is selected from sodium hydrogen carbonate, potassium hydrogen carbonate, and sodium carbonate.

* * * * *